United States Patent
Knauer

(10) Patent No.: US 11,976,094 B2
(45) Date of Patent: May 7, 2024

(54) METHOD FOR PREPARING PEPTIDES

(71) Applicant: Sulfotools GmbH, Darmstadt (DE)

(72) Inventor: Sascha Knauer, Darmstadt (DE)

(73) Assignee: Sulfotools GmbH, Darmstadt (DE)

( * ) Notice: Subject to any disclaimer, the term of this patent is extended or adjusted under 35 U.S.C. 154(b) by 113 days.

(21) Appl. No.: 17/705,607

(22) Filed: Mar. 28, 2022

(65) Prior Publication Data

US 2022/0220151 A1 Jul. 14, 2022

Related U.S. Application Data

(63) Continuation of application No. 16/766,423, filed as application No. PCT/EP2018/082403 on Nov. 23, 2018, now Pat. No. 11,319,340.

(30) Foreign Application Priority Data

Nov. 24, 2017 (DE) .......................... 102017127835.4

(51) Int. Cl.
| | | |
|---|---|---|
| *C07K 1/02* | (2006.01) | |
| *C07K 1/04* | (2006.01) | |
| *C07K 1/06* | (2006.01) | |
| *C07K 1/08* | (2006.01) | |
| *C07K 1/10* | (2006.01) | |
| *C07K 1/18* | (2006.01) | |

(52) U.S. Cl.
CPC ................ *C07K 1/061* (2013.01); *C07K 1/04* (2013.01); *C07K 1/042* (2013.01); *C07K 1/063* (2013.01); *C07K 1/08* (2013.01); *C07K 1/10* (2013.01); *C07K 1/02* (2013.01); *C07K 1/18* (2013.01)

(58) Field of Classification Search
CPC . C07K 1/02; C07K 1/04; C07K 1/042; C07K 1/063; C07K 1/08; C07K 1/082; C07K 1/084; C07K 1/086; C07K 1/088; C07K 1/10; C07K 1/18
See application file for complete search history.

(56) References Cited

U.S. PATENT DOCUMENTS

| | | | |
|---|---|---|---|
| 5,216,125 A | 6/1993 | Kouge | |
| 11,319,340 B2 * | 5/2022 | Knauer | ..................... C07K 1/08 |
| 2009/0099307 A1 | 4/2009 | Sharma | |
| 2017/0218010 A1 | 8/2017 | Knauer et al. | |

FOREIGN PATENT DOCUMENTS

| | | |
|---|---|---|
| WO | WO-01/46216 A2 | 6/2001 |
| WO | WO-2013/115813 A1 | 8/2013 |
| WO | WO-2016/050764 A1 | 4/2016 |

OTHER PUBLICATIONS

Fernández-Llamazares et al., "Tackling Lipophilicity of Peptide Drugs: Replacement of the Backbone N-Methyl Group of Cilengitide by N-Oligoethylene Glycol (N-OEG) Chains", Bioconjugate Chemistry, vol. 25, No. 1, Dec. 17, 2013, pp. 11-17.
Annathur et al., "Application of Arginine as an Efficient Eluent in Cation Exchange Chromatographic Purification of a PEGylated Peptide", Journal of Chromatography, vol. 1217, No. 24, Jun. 1, 2010, pp. 3783-3793.
Hojo et al., "2-(4-Sulfophenylsulfonyl)ethoxycarbonyl Group: A New Water-soluble N-protecting Group and its Application to Solid Phase Peptide Synthesis in Water", Tetrahedron Let., Elsevier, vol. 45, No. 50, Dec. 6, 2004, pp. 9293-9295.
International Search Report and Written Opinion in International Application No. PCT/EP2018/082403 dated Feb. 18, 2019, 17 pages.
Gutheil et al. N-to-C Solid-Phase Peptide and Peptide Trifluoromethylketone Synthesis Using Amino Acid tert-Butyl Esters. Chemical and Pharmaceutical Bulletin. 2002, vol. 50, No. 5, pp. 688-191. (Year: 2002).
Henkel et al. Investigations on Solid-Phase Peptide Synthesis in N-to-C Direction (Inverse Synthesis). Liebigs Ann./Recueil. 1997, pp. 2161-2168. (Year: 1997).
"Protein Research Technology", Yan Zhen et al., Fourth Military Medical University Press, Jan. 31, 2007, pp. 184-185.
Bodanszky, "Synthesis of Peptides by Aminolysis of Nitrophenyl Esters", Nature 175, Apr. 16, 1955, p. 685.
Bodanszky et al., "Synthesis of a Biologically Active Analog of Oxytocin, with Phenylalanine Replacing Tyrosine", Contribution From the Department of Biochemistry, Cornell University Medical College, vol. 81, Nov. 20, 1959, pp. 6072-6075.
Office Action in CN Application No. 201880086678.2 dated Nov. 29, 2023, 14 pages.

\* cited by examiner

*Primary Examiner* — Jeffrey E. Russel
(74) *Attorney, Agent, or Firm* — MARSHALL, GERSTEIN & BORUN LLP

(57) ABSTRACT

A method for preparing peptides is disclosed, the method comprising a step of forming a peptide bond wherein the carboxyl group of a first amino acid or first peptide is activated and an amino group of the first activated amino acid or first peptide is protected by a protecting group having a water-solubility enhancing group and the activated carboxyl group of the first amino acid or first peptide is reacted with an amino group of a second amino acid or second peptide wherein said carboxyl group of the first amino acid or first peptide is activated in the absence of the second amino acid or second peptide. Peptides comprising a protecting group having a water-solubility enhancing group being bound to the amino group and an activated or free carboxyl group are also disclosed.

22 Claims, No Drawings
Specification includes a Sequence Listing.

METHOD FOR PREPARING PEPTIDES

CROSS-REFERENCE TO RELATED APPLICATIONS

This application is a continuation of U.S. application Ser. No. 16/766,423 filed May 22, 2020, which is the U.S. national stage of PCT/EP2018/082403 filed Nov. 23, 2018, which claims the priority benefit of German application No. 102017127835.4 filed on Nov. 24, 2017. The disclosure of U.S. application Ser. No. 16/766,423 is hereby incorporated by reference herein in its entirety.

The Sequence Listing, which is a part of the present disclosure, is submitted concurrently with the specification as a text file. The name of the text file containing the sequence listing is "55488A_Seqlisting.txt", which was created on Mar. 7, 2022 and is 966 bytes in size. The subject matter of the sequence listing is incorporated herein in its entirety by reference.

BACKGROUND OF THE INVENTION

Field of the Invention

The present invention relates to an improved method for preparing peptides, and to peptides being obtainable by the method.

Related Technology

Peptides are linked chains of amino acids and represent the precursors of proteins. Peptides and proteins are the elementary components of all living systems and are involved in a variety of processes of life. They have many applications in medical and biological sciences. As a consequence, the capability to synthesize peptides and proteins is of high significance to human life.

Hence, the synthetic production of peptides is of significant interest. Peptides are conventionally synthesized by coupling the carboxyl group (C-terminus) of one amino acid to the amino group or N-terminus of another.

In general, the chemical synthesis starts from the C-terminal amino acid of the chain. In addition, it requires an additional chemical group to protect the C-terminus of the first amino acid. The process of coupling individual amino acids can be accomplished by employment of different chemical coupling reagents, resulting in an activated carboxyl group. After formation of the amide bond, the Nα-protecting group is removed; conditions for this are depending on the used protecting group. However, solution phase chemistry is slow and labour-intensive because the product has to be isolated from the reaction solution manually after each step by a purification step (extraction, washing or crystallisation). Despite the disadvantages of the method, solution phase chemistry is still the method of choice for production of short peptides, for example di-, tri- or tetrapeptides, longer sequences are possible with fragment condensation procedures. That's because Boc or CBz protected amino acids are less expensive raw materials than Fmoc-amino acids, and the solution phase chemistry has nearly unlimited synthesis capacity.

Solid-phase peptide synthesis (SPPS) was introduced by Merrifield et al. in 1963 with the intent to overcome the intermediate purification problems associated with peptide assembly in solution (see Stewart and Young, Solid Phase Peptide Synthesis (*Pierce Chemical Co.*, 2d ed., 1984), Chan and White, Fmoc Solid Phase Peptide Synthesis: A Practical Approach (Oxford University Press, 2000)). Upon solid-phase synthesis, amino acids are consecutively coupled to result in a peptide possessing the desired sequence while the C-terminus is anchored to an insoluble polymeric support (solid phase). Once the desired sequence has been assembled, the peptide is cleaved from the solid support.

This synthetic scheme requires the protection of the α-amino group of the incoming amino acid in order to avoid self-polymerization. The standard protecting groups for α-amino functions are the acid-labile tert-butyloxycarbonyl (Boc) group, the base-labile fluorenylmethyloxycarbonyl (Fmoc) group and the allyloxycarbonyl (Alloc) group which is removed under neutral conditions with Pd catalysis in the presence of $PhSiH_3$ as scavenger for the allyl system.

Methods for solid-phase peptide synthesis following any of the three above-mentioned α-amino protection schemes generally require additional protection of reactive side chains of the constituent amino acids from unwanted chemical transformations. Therefore, it is necessary that these protecting groups are resistant to the agents used during the coupling cycle. Additionally, the linkage between the growing peptide chain and the solid-phase support has to be stable towards the conditions of α-amino deprotection and chain assembly.

In the case of the Fmoc-based α-amino protection, the side-chain groups should be resistant to the basic reagents used to remove the Fmoc moiety. The side-chain protecting groups are generally removed by mild acidic reagents after the peptide chain has been assembled. These side-chain protecting groups are generally cleaved by anhydrous HF, trifluoromethanesulfonic acid or trifluoro acetic acid (TFA) after the desired peptide chain has been assembled.

The peptide assembly procedure is typically performed in polar aprotic organic solvents such as dimethyl formamide (DMF), N-methylpyrrolidone (NMP), dimethyl sulfoxide (DMSO) and dichloromethane (DCM), or a mixture of these organic solvents because of the strong hydrophobic character of the α-amino protecting groups Fmoc and Boc, which are insoluble in water and which are frequently used in SPPS. Additionally, the side-chain protecting groups commonly used in SPPS are usually hydrophobic and render the amino acid insoluble in water.

SPPS approaches applying Fmoc and Boc protection are widely used but suffer from the need for the previously mentioned organic solvents which are costly and toxic. DMF, for example, comes with considerable health and environmental risks; it has been linked to cancer in humans, and it is suspected to cause birth defects. Hence, the use of these toxic solvents requires special technical equipment and precautions, as e.g. performing the reaction under the fume hood and handling by highly specialized personnel. In addition, the disposal of the used solvent is problematic and expensive. As a consequence, SPPS using organic solvents is expensive and restricted to specialised laboratories with special equipment for organic chemistry synthesis.

As an attempt to overcome this problem, Hojo et al. proposed the use of water-soluble protecting groups (*Chem. Pharm. Bull.* 2004, 52, 422-427 and *Tetrahedron Lett.* 2004, 45, 9293.) They developed several protecting groups for this purpose, among them 2-(Phenyl(methyl)sulfonyl)ethyloxycarbonyl tetrathioborate (Pms), Ethanesulfonylethoxycarbonyl (Esc), and 2-(4-Sulfophenylsulfonyl)ethoxy carbonyl (Sps). In WO 2013 115813 A1 the CEM Corporation claims the deprotection of α,β-unsaturated sulfones in water or aqueous systems and their usage in water-based SPPS.

Furthermore, WO 2016/050764 A1 describes a water-based peptide synthesis.

The methods mentioned above can be used to synthesize peptides. However, it is a permanent desire to improve these methods.

SUMMARY

Therefore, it is an object of the invention to provide an improved method for peptide synthesis in general. The method should be applicable to liquid and solid-phase peptide synthesis.

According to a specific object of the present invention, the method should provide a high yield. Furthermore, the synthesis of the peptide should be performed at low costs. A further object of the present invention is a method having a low racemization of the amino acid units being incorporated into the peptide chain. In addition, the method for preparing peptides should be executed with low waste and with high environmental sustainability.

Furthermore, the present method should be performable using known apparatus in order to achieve a high acceptability. Moreover, the method should have a low impact on the environment. Preferably, only environmentally acceptable solvents and compounds should be used and/or the solvents should be recovered easily that no critical impact to the environment should be expectable.

These objects and further objects which are not stated explicitly but which are immediately derivable or discernible from the connections discussed herein by way of introduction are solved by a method for preparing peptides comprising the step of forming a peptide bond having all features of claim 1.

The present invention accordingly provides a method for preparing peptides comprising the step of forming a peptide bond characterized in that the carboxyl group of a first amino acid or first peptide is activated and an amino group of the first activated amino acid or first peptide is protected, preferably by a protecting group having a water-solubility enhancing group or by a solid phase, and the activated carboxyl group of the first amino acid or first peptide is reacted with an amino group of a second amino acid or second peptide wherein said carboxyl group of the first amino acid or first peptide is activated in the absence of the second amino acid or second peptide.

It is thus possible in an unforeseeable manner to improve the prior art methods for preparing peptides as mentioned above.

The peptides can be obtained very inexpensively. Surprisingly, the peptides obtained contain only very small amounts of by-products, especially a low racemization of the amino acid units being incorporated into the peptide chain can be achieved by the present method.

In addition, the process according to the invention enables a particularly selective preparation of the peptides. Furthermore, the method according to the invention can be performed in a simple and inexpensive manner, the product being obtainable in high yields and, viewed overall, with low energy consumption.

In addition, the method for preparing peptides can be executed with low waste and with high environmental sustainability.

Furthermore, the present method can be performable using known apparatus in order to achieve a high acceptability. Moreover, the methods have a low impact on the environment. Preferably, only environmentally acceptable solvents and compounds are used and/or the solvents can be recovered easily such that no critical impact to the environment is expectable.

DETAILED DESCRIPTION

According to a first embodiment of the invention, an amino group of the first activated amino acid or first peptide is protected by a protecting group having a water-solubility enhancing group. In addition thereto, the first amino acid or first peptide preferably comprises additional protecting groups. Preferably, the functional group to be protected is preferably selected from amine, alcohol, thiol, carboxyl, phosphono and/or seleno groups.

In preferred embodiments the water-solubility enhancing functional group is selected from the charged functional groups $SO_3^-$, $PO_3^{2-}$, $OSO_3^-$ ester, $OPO_3^{2-}$ ester and $N(CH_3)_3^+$. Using charged functional groups as the water-solubility enhancing functional group has been proven useful for increasing solubility in environmentally friendly solvents, e.g. water-solubility more efficiently than the uncharged functional groups.

According to a second embodiment of the invention, an amino group of the first activated amino acid or first peptide is protected by solid phase. Protection by a solid phase is preferably achieved by a covalent bond of the amino group of the first activated amino acid or first peptide to a solid phase. Preferably, the covalent bond of the amino group of the first activated amino acid or first peptide to the solid phase is cleavable. Consequently, the peptide or protein achieved with the present method can be released from the solid phase by a cleavage reaction as described in more detail below. In addition thereto, the first amino acid or first peptide preferably comprises additional protecting groups. Preferably, the functional group to be protected is preferably selected from amine, alcohol, thiol, carboxyl, phosphono and/or seleno groups.

The protection of the amino group of the first activated amino acid or first peptide by a protecting group having a water-solubility enhancing group is preferred over a protection using a solid phase in view of sustainability, costs and efficiency. On the other hand, a protection of the amino group of the first activated amino acid or first peptide by a solid phase provides improvements regarding the production of peptides having a high number of amino acid units.

Preferably, the forming of the peptide bond is achieved using an environmentally friendly solvent. The forming of the peptide bond includes the activation of the carboxyl group of said first amino acid or first peptide, the reaction of the activated carboxyl group of the first amino acid or first peptide with an amino group of a second amino acid or second peptide or both steps. Conventionally, peptide synthesis is achieved in solvents which are critical to the environment or health. These solvents include dimethylformamide (DMF) and N-methyl-2-pyrrolidone (NMP). Although these solvents can be used to perform the present method, the present invention is not limited thereto but environmentally friendly solvents can be used which provides further cost advantages and lower precautions based on environmental standards. Therefore, one of the advantages of the invention is the utilization of an amino acid and/or peptide that is soluble in an environmentally friendly solvent in its protected form.

As used herein, the term "soluble in an environmentally friendly solvent in its protected form" means that the composition has the degree of solubility necessary for the desired reaction to proceed in a solvent system. As in the case with any composition, the term "soluble" does not imply unlimited solubility in any or all amounts.

Preferably the environmental friendliness of the solvents is based on their impact on health or the environment. Substances that are listed by the European Chemicals Agency (ECHA) as substances of very high concern (SVHCs) or on the candidate list of substances of very high concern are not classified as environmentally friendly solvents. In order to avoid using harmful organic solvents that may have serious and often irreversible effects on human health and the environment, all solvents listed by the ECHA as SVHCs should be avoided (state 14.11.2017).

According to a preferred embodiment, the environmentally friendly solvent preferably has a DNEL value of at least 5 mg/m$^3$, more preferably at least 10 mg/m$^3$, more preferably of at least 20 mg/m$^3$, more preferably at least 40 mg/m$^3$, more preferably at least 45 mg/m$^3$, more preferably at least 60 mg/m$^3$, more preferably at least 100 mg/m$^3$, more preferably at least 120 mg/m$^3$, and even more preferably of at least 200 mg/m$^3$ (inhalation, systemic, as provided by the ECHA state 14.11.2017).

In a specific embodiment, said environmentally friendly solvent preferably has a lethal dose LD50 of at least 0.1 g/kg, preferably of at least 0.5 g/kg, more preferably of at least 1.0 g/kg, more preferably of at least 1.5 g/kg, more preferably of at least 2 g/kg and even more preferably of at least 2.5 g/kg (oral, rat).

Preferred solvents, more preferably environmentally friendly solvents include protic solvents, such as water, primary, secondary and/or tertiary alcohols, non-protic solvents such as ketones, nitriles, lactones, lactams, carbon acid amides, carbon acid ester, ether, urea derivatives, sulfoxides, sulfones, carbonate ester. Preferred examples of non-protic solvents are e.g. dimethylacetamide, ethyl methyl ketone, acetone, methyl isopropyl ketone, methyl isobutyl ketone, methyl n-butyl ketone, methyl t-butyl ketone, methyl isoamyl ketone, dimethyl sulfoxide, hexamethylphosphoric triamide, tetrahydrofuran, dioxane, dimethoxyethane, diethylene glycol, dimethyl ether, ethyl acetate, tertiary butyl acetate, or mixture(s) thereof.

A protic solvent is a solvent that has a hydrogen atom bound to an oxygen (as in a hydroxyl group) or a nitrogen (as in an amine group). Non-protic solvents are solvents which do not include a hydrogen atom bound to an oxygen (as in a hydroxyl group) or a nitrogen (as in an amine group). Therefore, a ketone is a non-protic solvent although some isomers (enol isomer) may include such hydrogen atoms. However, based on the low percentage of these isomers being formed, these isomers have to be neglected with regard to the present invention.

The present invention can be achieved using a protic solvent, such as water, primary, secondary and/or tertiary alcohols. Primary and secondary amines should not be used as a solvent based on the coupling reaction for forming a peptide bond. Preferred alcohols include methanol, ethanol, isopropanol, 2-propanol, n-propanol, n-butanol, isobutanol, sec-butanol, tert-butanol, or a mixture thereof. Protic solvents provide advantages regarding costs and lower precautions based on environmental standards. Regarding protic solvents water is especially preferred. In addition to the costs advantages and high environmental acceptance, water provides improvements regarding safety, especially low flammability and combustibility can be achieved by solvents comprising water. Furthermore, water provides higher yield in view of other protic solvents such as alcohols, especially primary alcohols.

In an embodiment of the present invention, the solvent, preferably the environmentally friendly solvent preferably comprises at least 5% by weight, more preferably at least 10% by weight, even more preferably at least 25% by weight of a protic solvent, preferably water based on the total weight of the solvent, preferably the environmentally friendly solvent.

In a further embodiment of the present invention, the solvent, preferably the environmentally friendly solvent preferably comprises at least 5% by weight, more preferably at least 10% by weight, even more preferably at least 25% by weight of a protic solvent, preferably water, based on the total weight of the solvent, preferably the environmentally friendly solvent.

Surprising improvements can be achieved by a solvent, preferably an environmentally friendly solvent comprising a non-protic organic solvent and/or a secondary and/or tertiary alcohol, preferably non-protic organic solvent and/or a tertiary alcohol, more preferably a non-protic organic solvent. The use of a non-protic organic solvent and/or a secondary and/or tertiary alcohol provides astonishing improvements in yield. Furthermore, the use of non-protic solvents provides a higher degree of conversion. Therefore, longer peptide chains are achievable at a considerable yield. Furthermore, the activation of an amino acid or peptide as mentioned above and below is easier and the activated amino acid or peptide is more stable. Therefore, lower amounts of activation agent can be used. In addition, further advantages can be achieved if the method is performed on an ion exchanger as mentioned above and below. Preferably, the ion exchanger is used in a method wherein an amino group of the first activated amino acid or first peptide is protected by a protecting group having a water-solubility enhancing group. Using a non-protic organic solvent and/or a secondary and/or tertiary alcohol in combination with an ion exchanger provides improvements in yield of the peptides prepared. These improvements can be increased by increasing the amount of non-protic organic solvent. These improvements are achieved by using a solvent, preferably an environmentally friendly solvent comprising a non-protic organic solvent and/or a secondary and/or tertiary alcohol, preferably non-protic organic solvent and/or a tertiary alcohol, more preferably a non-protic organic solvent for the activation of the carboxyl group of said first amino acid or first peptide. Furthermore, these improvements are achieved by using a solvent, preferably an environmentally friendly solvent comprising a non-protic organic solvent and/or a secondary and/or tertiary alcohol, preferably non-protic organic solvent and/or a tertiary alcohol, more preferably a non-protic organic solvent for the reaction of the activated carboxyl group of the first amino acid or first peptide with an amino group of a second amino acid or second peptide as mentioned above and below. In a very preferred embodiment, the activation of the carboxyl group of said first amino acid or first peptide and the reaction of the activated carboxyl group of the first amino acid or first peptide with an amino group of a second amino acid or second peptide bond as mentioned above and below are achieved by using a solvent, preferably an environmentally friendly solvent comprising a non-protic organic solvent and/or a secondary and/or tertiary alcohol, preferably non-protic organic solvent and/or a tertiary alcohol, more preferably a non-protic organic solvent.

In an embodiment of the present invention, the solvent, preferably the environmentally friendly solvent preferably comprises at least 5% by weight, more preferably at least 10% by weight, even more preferably at least 25% by weight of a non-protic organic solvent and/or a secondary and/or tertiary alcohol, preferably non-protic organic solvent based on the total weight of the solvent, preferably the environmentally friendly solvent.

In a particularly appropriate variant said solvent, preferably said environmentally friendly solvent comprises a non-protic organic solvent as a first solvent and water and/or alcohol as a second solvent, preferably a non-protic organic solvent and water.

In preferred embodiments said solvent, preferably said environmentally friendly solvent comprises 5 to 95% by weight, preferably 10 to 70% by weight of said second solvent, based on the total weight of the solvent, preferably the environmentally friendly solvent. Furthermore, said solvent, preferably said environmentally friendly solvent preferably comprises 5 to 95% by weight, more preferably 10 to 90% by weight, even more preferably 30 to 70% by weight of said first solvent, based on the total weight of the solvent, preferably the environmentally friendly solvent.

Surprisingly, the use of non-protic organic solvents having a low polarity such as dimethylacetamide, ethyl methyl ketone, acetone, methyl isopropyl ketone, methyl isobutyl ketone, methyl n-butyl ketone, methyl t-butyl ketone, methyl isoamyl ketone, dimethyl sulfoxide, hexamethylphosphoric triamide, tetrahydrofuran, dioxane, dimethoxyethane, diethylene glycol, dimethyl ether, ethyl acetate, tertiary butyl acetate, or mixture(s) thereof and/or protic solvents such as water and alcohols provide astonishing improvements regarding the racemization of the peptides formed. In contrast thereto the use of polar aprotic organic solvents, such as dimethylformamide (DMF) and N-methyl-2-pyrrolidone (NMP) provide a higher racemization of the peptides formed. Preferably, the polarity is defined as the dipole moment of the molecule. Preferably, the dipole of the aprotic organic solvent is at most $12.6 \cdot 10^{-30}$ Cm, more preferably at most $12.5 \cdot 10^{-30}$ Cm, preferably measured at 25° C. and 1023 mbar by the measurement of the dielectric constant using the Debye equation and/or measuring the Starr effect, preferably by measuring the dielectric constant. In a preferred embodiment, the racemization of the peptides formed can be avoided or reduced by adding and/or using a protic solvent, more preferably water. The addition of a protic solvent, preferably water reduces the racemization of the peptides formed if a polar aprotic organic solvent is used.

Preferably, the forming of the peptide bond is achieved in solution having no strong basic condition, preferably at a pH below 12, more preferably at a pH below 10 measured by adding water to the solution at 25° C. according to the professional methods known, e.g. pH-electrodes. The measured sample preferably comprises at least 80% by weight water. Preferably, pH-electrodes are calibrated using two, three or more buffer solutions having a specified pH value. Performing the reaction in solution having no strong basic condition provides astonishing improvements regarding the racemization of the peptides formed.

According to the invention, the carboxyl group of a first amino acid or first peptide is activated and the activated carboxyl group of the first amino acid or first peptide is reacted with an amino group of a second amino acid or second peptide.

In a preferred embodiment carboxyl group of a first amino acid or first peptide is activated by a coupling agent.

Preferably, the coupling agent is a combination of a carbodiimide, preferably diisopropylcarbodiimide (DIC), dicyclohexylcarbodiimid (DCC), 1-ethyl-3-(3-dimethylaminopropyl)carbodiimide (EDC), 2-(((ethylimino)methylene) amino)-2-methylpropane-1-sulfonate (ESC) and 2,2'-(methanediylidenebis(azanylylidene)) bis(2-methylpropane-1-sulfonate) (DSC), and an active ester forming compound, preferably 1-hydroxybenzotriazole (HOBt), 1-hydroxy-7-azabenzotriazole (HOAt), N-hydroxysuccinimide (NHS), ethylcyano(hydroxyimino)acetate (Oxyma), hydroxy-3,4-dihydro-4-oxo-1,2,3-benzotriazine (HOOBt), 4-dimethylaminopyridine (DMAP), 2-Hydroxypyridine-N-oxide (HOPO). Coupling agent could also be based on phosphonium- and the aminium-(imonium-) type reagents such as (benzotriazol-1-yloxy)tris(dimethylamino) phosphonium hexafluorophosphate (BOP), (benzotriazol-1-yloxy) tripyrrolidino phosphonium hexafluorophosphate (PyBOP), bromotri(pyrrolidino)phosphonium hexafluorophosphate (PyBrOP), ethyl cyano(hydroxyimino)acetato-O2)-tri-(1-pyrrolidinyl)-phosphonium hexafluorophosphate (PyOxim), (3-(diethoxyphosphoryloxy)-1,2,3-benzotriazin-4(3H)-one) (DEPBT), (1H-benzotriazol-1-yloxy)-N,N-dimethylmethaniminium hexachloroantimonate (BOMI), 5-(1H-benzotriazol-1-yloxy)-3,4-dihydro-1-methyl 2H-pyrrolium hexachloroantimonate (BDMP), 5-(7-azabenzotriazol-1-yloxy)-3,4-dihydro-1-methyl-2H-pyrrolium hexachloroantimonate (AOMP), 5-(pentafluorophenyloxy)-3,4-dihydro-1-methyl-2H-pyrrolium hexachloroantimonate (FOMP), 5-(3',4'-dihydro-4'-oxo-1', 2',3'-benzotriazin-3'-yloxy)-3,4-dihydro-1-methyl 2H-pyrrolium hexachloroantimonate (DOMP), 1-(1H-benzotriazol-1-yloxy)phenylmethylene pyrrolidinium hexachloroantimonate (BPMP), 5-(succinimidyloxy)-3,4-dihydro-1-methyl-2H-pyrrolium hexachloroantimonate (SOMP), tetramethylfluoroformamidinium hexafluorophosphate (TFFH), O-(benzotriazol-1-yl)-1,1,3,3-tetramethyl-uronium hexafluorophosphate (HBTU), O-benzotriazol-1-yl-1,1,3,3-tetramethyluronium tetrafluoroborate (TBTU), 1-[Bis(dimethylamino) methylene]-1H-1,2,3-triazolo[4,5-b]pyridinium 3-oxid hexafluorophosphate (HATU), (2-(6-chloro-1-H-benzotriazol-1-yl)-1,1,3,3-tetramethylaminium) hexafluorophosphate (HCTU), O-(7-azabenzotriazol-1-yl)-1,1,3,3-tetra-methyluronium tetrafluoroborate (TATU), 2-(5-norbornene-2,3-dicarboximido)-1,1,3,3-tetramethyluronium tetrafluoroborate (TNTU), 1-((dimethyl-amino)(dimethyliminio)methoxy)-2-hydroxypyridinium tetrafluoroborate (TPTU), O-(cyano(ethoxycarbonyl)methylenamino)-1,1,3,3-tetramethyluronium tetrafluoroborate (TOTU), 2-(3,4-dihydro-4-oxo-1,2,3-benzotriazin-3-yl)-1,1,3,3-tetramethyluronium tetrafluoroborate (TDBTU), 1-[1-(cyano-2-ethoxy-2-oxoethylideneaminooxy)-dimethylamino-morpholino] uronium hexafluorophosphate (COMU), 4-{[1,3-dimethyl-2,4,6-trioxotetrahydropyrimidin-5(6H)ylidenaminooxy] (dimethylamino)-methylen}morpholin-4-iumhexafluorophosphat (COMBU), N-{[1,3-dimethyl-2,4,6-trioxotetrahydropyrimidin-5(6H)-ylidenaminooxy] (dimethylamino)methylen}-N-methylmethanaminiumhexafluorophosphat (TOMBU), 2-succinimido-1,1,3,3-tetramethyluronium tetrafluoroborate (TSTU). Also miscellaneous coupling reagents like EEDQ (N-ethoxycarbonyl-2-ethoxy-1,2-dihydroquinoline) and DMTMM (4-(4,6-dimethoxy-1,3,5-triazin-2-yl)-4-methylmorpholinium salts) and other condensation products of substituted cyanuric chloride with bases.

In a preferred embodiment, a carboxyl group of a first amino acid or first peptide is activated by a coupling agent. Preferably, an excess of coupling agent is used, preferably the coupling agent is used in at least two-fold molar amount, more preferably in at least three-fold molar amount in relation to the first amino acid or first peptide. An excess of coupling agent is preferably removed from the reaction mixture before the second amino acid or second peptide is added to the activated first amino acid or first peptide. In an alternative embodiment, the coupling agent is used in an equimolar amount or below in order to achieve that all of the added coupling agent react with the first amino acid or first peptide. In that case, no excess of coupling agent remains in the reaction mixture.

In an embodiment of the present invention, it can be provided that the first amino acid or first peptide is preferably ionically contacted with an ion exchanger. The contacting of the first amino acid or first peptide can be achieved at any step of the present method as mentioned above and below. Preferably, the first amino acid or first peptide being ionically contacted with an ion exchanger comprises at least one protecting group having a water-solubility enhancing group, more preferably an ionic water-solubility enhancing group.

In a preferred embodiment, the carboxyl group of a first amino acid or first peptide is preferably activated by a coupling agent while the first amino acid or first peptide is ionically bound to an ion exchanger. Preferably, the first amino acid or first peptide being ionically bound to an ion exchanger comprises at least one protecting group having a water-solubility enhancing group, more preferably an ionic water-solubility enhancing group. In a variant of the present method, excess of coupling agent is preferably removed from the ion exchanger before a second amino acid or second peptide is added to the ion exchanger.

In a further preferred embodiment, said forming of a peptide bond is achieved while an amino acid or a peptide is ionically bound to an ion exchanger. Preferably, the first amino acid or first peptide being ionically bound to an ion exchanger comprises at least one protecting group having a water-solubility enhancing group, more preferably an ionic water-solubility enhancing group. The ionically bounding to the ion exchanger may include any step of forming the peptide bond comprising the activation of the carboxyl group of an amino acid or peptide, the reaction of the activated carboxyl group of an amino acid or peptide with an amino group of another amino acid or another peptide or both steps. Preferably, said forming of a peptide bond is achieved while an amino acid or peptide is not covalently bound to an ion exchanger.

According to the second embodiment of the present invention, the amino group of the first activated amino acid or first peptide is protected by solid phase. The solid phase (solid support) is preferably an insoluble resin, preferably being based on crosslinked polystyrene, polyacryl, polyphenol, polysaccharide, polyamide or polylysine. Preferably, the covalent bonding of the amino group of the first activated amino acid or first peptide to the solid support is achieved by a linking group. The linking group preferably provides a cleavable link of the growing peptide to the solid phase. The cleavage is preferably achieved using a cleaving composition as mentioned below. The use of solid supports for preparing peptides is well known in a synthesis wherein the C-terminus of the first amino acid is anchored via the N-terminus and further amino acids are coupled to the N-terminus of the peptide being anchored to the solid support. Solid supports having reactive groups which can from a covalent bond with the amino group of the first activated amino acid or first peptide are commercially available. The reactive groups of the solid phase being useful for forming a linkage with the amino group of the first activated amino acid or first peptide are well known in the art. The person skilled in the art will choose the groups depending on the reaction conditions and the required stability and cleavability of the bonding.

Preferably, a carboxyl group of the second amino acid or second peptide being reacted with said first activated amino acid or first peptide is not protected. In a preferred embodiment, the protection of a carboxyl group of the second amino acid or second peptide can be avoided. Such embodiment provides astonishing cost advantages. Protection may be achieved by a protection group or by bonding to a solid phase.

In a preferred embodiment, the synthesis of a peptide is build up via the carboxyl group of an amino acid or peptide and a carboxyl group of the second amino acid or second peptide being reacted with said first activated amino acid or first peptide is not protected wherein the method comprises the steps of activating a first amino acid or first peptide, removing an excess of coupling agent, adding a second amino acid or second peptide to the first activated amino acid or first peptide and reacting the second amino acid or second peptide with the first activated amino acid or first peptide and forming a peptide bond, removing residues of the reaction by a washing step. These steps can be repeated in order to achieve a desired peptide.

In an alternative embodiment, the synthesis of a peptide is build up via the carboxyl group of an amino acid or peptide and a carboxyl group of the second amino acid or second peptide being reacted with said first activated amino acid or first peptide is protected wherein the method comprises the steps of activating a first amino acid or first peptide, adding a second amino acid or second peptide having a protected carboxyl group to the first activated amino acid or first peptide and reacting the second amino acid or second peptide with the first activated amino acid or first peptide and forming a peptide bond, optionally capping unreacted carboxyl groups of first amino acid or first peptide, deprotecting the carboxyl group of the second amino acid or second peptide. Optionally residues of the reaction are removed by a washing step being performed between the steps mentioned. These steps can be repeated in order to achieve a desired peptide.

It is preferred that said second amino acid or second peptide is preferably a peptide having at least two amino acid units, more preferably a peptide having at least four amino acid units, even more preferably a peptide having at least six amino acid units. Such embodiment provides unforeseeably improvements regarding yield of the peptides being prepared and provides cost improvements.

According to a preferred embodiment, the amino group of the first activated amino acid or first peptide is protected by a protecting group having a water-solubility enhancing group being ionically bound to an ion exchanger, preferably the water-solubility enhancing group comprises an ionic group being ionically bound to an ion exchanger.

The type of the protecting group being used in order to achieve an ionic bound to the ion exchanger is not critical.

Preferably, the ion exchanger is an ion exchange resin, preferably being based on crosslinked polystyrene, polyacryl, polyphenol or polysaccharide and having a functional group or the ion exchanger is a mineral ion exchanger, preferably based on silica.

Preferably, said functional group of the ion exchange resin is a tetra alkyl ammonium group ($-NR_3^+$), a primary, secondary or tertiary ammonium group ($-NH_2$, $-NHR$, $-NR_2$), a carboxylic group ($-COO^-$), sulfonic group ($-SO_3^-$), wherein R is an alkyl group having 1 to 10 carbon atoms.

In the present description, conventional terms regarding the description of the ion exchanger are used. Consequently, a basic ion exchanger is a solid having the ability to exchange anions. An acidic ion exchanger is a solid having the ability to exchange cations.

In a specific embodiment, a basic exchange resin is used and the amino acid or peptide comprises an anionic water-solubility enhancing group, preferably weak basic exchange resin is used comprising primary, secondary and/or tertiary amino groups. Preferably, an anionic ion exchanger is used.

In another embodiment of the present invention, a cationic ion exchanger is used. Preferably an acid exchange resin is used and the amino acid or peptide comprises a cationic water-solubility enhancing group.

The present amino acid or peptide preferably comprises a protecting group having a water-solubility enhancing group. The expression "water-solubility enhancing group" describes a group providing improved water solubility to a protecting group. In principle every conventional protecting group being used in peptide synthesis can be used which have a group or a modification providing improved water-solubility. These protecting groups having a water-solubility enhancing group include compounds as mentioned by Hojo et al. proposed (*Chem. Pharm. Bull.* 2004, 52, 422-427 and *Tetrahedron Lett.* 2004, 45, 9293.) and in WO 2013 115813 A1, as e.g. 2-(phenyl(methyl)sulfonyl)ethyloxycarbonyl tetrathioborate (Pms), ethanesulfonylethoxycarbonyl (Esc), and 2-(4-sulfophenylsulfonyl)ethoxy carbonyl (Sps).

In a preferred embodiment, the protecting group having a water-solubility enhancing group comprises a back bone structure and a linking group being derived from a reactive group.

In a specific embodiment, the protection of said amino acid or peptide is preferably achieved by reacting an amino acid or a peptide with a protective agent comprising
  I. a backbone structure,
  II. at least one water-solubility enhancing group and
  III. at least one reactive group,
  wherein the backbone structure comprises a moiety selected from the group consisting of 9-methylfluorene, t-butane and/or mono-, di or triphenylmethane,
  wherein the water-solubility enhancing group is selected from the group consisting of $SO_3^-$, $PO_3^{2-}$, $N(CH_3)_2$, $N(CH_3)_3^+$, CN, $OSO_3^-$ ester, $OPO_3^{2-}$ ester and combinations thereof, and
  wherein the water-solubility enhancing group and the reactive group are attached to the backbone structure via at least one covalent bond.

The protective agent may comprise one or more water-solubility enhancing functional groups, in preferred embodiments the protective agent comprises more than one water-solubility enhancing functional group. In further preferred embodiments the protective agent comprises at least two water-solubility enhancing functional groups. In other preferred embodiments the protective agent comprises from 1 to 8, 2 to 7, or 3 to 4 water-solubility enhancing functional groups. The inventors have found out that it may be useful to have more than one water-solubility enhancing functional group in the protective agent molecule because the water-solubility is increased to a greater extent. In embodiments where the backbone structure is t-butane or phenylmethane one water solubility enhancing functional group may be sufficient.

In preferred embodiments of this invention, the protective agent comprises water-solubility enhancing functional groups that are all of the same kind, in particular, all of the kind $SO_3^-$. In alternative embodiments, the protective agent comprises water-solubility enhancing functional groups of different kinds. In as far as the water-solubility enhancing functional group is $SO_3^-$, it is preferred that the protective agent comprises at least 2 of these functional groups. Synthesis of the protective agent can be more efficient and easier, if the water-solubility enhancing functional groups are all of the same kind.

The backbone structure comprises a moiety selected from the group consisting of 9-methylfluorene, t-butane and/or mono-, di- or triphenylmethane. In preferred embodiments, the backbone structure is selected from 9-methylfluorene and t-butane.

The reactive group is suitable, i.e. has the required chemical reactivity to undergo a chemical reaction with the functional group to be protected. It is preferably selected from the group consisting of oxycarbonyl halogenide, oxycarbonyl O-succinimide, oxycarbonyl Oxyma ester, oxycarbonyl anhydride, halogenide, oxymethyl halogenide, hydroxide and thiol groups. When the backbone structure is 9-methylfluorene the reactive group is preferably selected from oxycarbonyl halogenide, oxycarbonyl Oxyma ester and oxycarbonyl O-succinimide. When the backbone structure is t-butane the reactive group is preferably selected from hydroxide, halogenide, thiol, oxycarbonyl O-succinimide and oxycarbonyl anhydride. When the backbone structure is selected from mono-, di- and triphenylmethane the reactive group is preferably selected from halogenide, oxymethyl halogenide and oxycarbonyl halogenide.

Preferred protective agents having the 9-methylfluorene backbone structure of the present invention can be illustrated by the following general formula 1:

General Formula 1

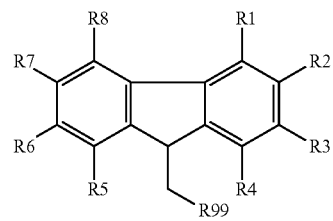

wherein R1 to R8 are independently selected from hydrogen, $SO_3^-$, $PO_3^{2-}$, $N(CH_3)_2$, $N(CH_3)_3^+$, $OSO_3^-$ ester, $OPO_3^{2-}$ ester and CN with the proviso that at least one, preferably at least two of R1 to R8 is selected from $SO_3^-$, $PO_3^{2-}$, $N(CH_3)_2$, $N(CH_3)_3^+$, $OSO_3^-$ ester, $OPO_3^{2-}$ ester and CN. In preferred embodiments all of R1 to R8 that are not $SO_3^-$, $PO_3^{2-}$, $N(CH_3)_2$, $N(CH_3)_3^+$, $OSO_3^-$ ester, $OPO_3^{2-}$ ester or CN are hydrogen.

R99 is preferably selected from the group consisting of oxycarbonyl halogenide, oxycarbonyl O-succinimide, oxycarbonyl Oxyma ester, oxycarbonyl anhydride, halogenide, oxymethyl halogenide, hydroxide and thiol groups, wherein R99 is preferably selected from oxycarbonyl halogenide, oxycarbonyl Oxyma ester and oxycarbonyl O-succinimide.

In preferred embodiments R2 and R7 are selected from $SO_3^-$, $PO_3^{2-}$, $N(CH_3)_2$, $N(CH_3)_3^+$, $OSO_3^-$ ester, $OPO_3^{2-}$ ester and CN, in particular R2 and R7 are $SO_3^-$. Preferably, R1, R3 to R6 and R8 are hydrogen.

In preferred embodiments R3 and R6 are selected from $SO_3^-$, $PO_3^{2-}$, $N(CH_3)_2$, $N(CH_3)_3^+$, $OSO_3^-$ ester, $OPO_3^{2-}$ ester and CN, in particular R3 and R6 are $SO_3^-$. Preferably, R1, R2, R4, R5, R7 and R8 are hydrogen.

In preferred embodiments R2 and R6 are selected from $SO_3^-$, $PO_3^{2-}$, $N(CH_3)_2$, $N(CH_3)_3^+$, $OSO_3^-$ ester, $OPO_3^{2-}$ ester and CN, in particular R2 and R6 are $SO_3^-$. Preferably, R1, R3, R4, R5, R7 and R8 are hydrogen.

Preferred protective agents having the 9-methylfluorene backbone structure of the present invention are shown in the following table 1. The compounds listed in the table are in no way limiting the scope of the present invention. They constitute illustrative and preferable protective agents according to this invention.

TABLE 1

| # | Protective agent | Backbone | $H_2O$ solubility enhancing group | reactive group | Protected group |
|---|---|---|---|---|---|
| 1 | | 9-methylfluorene | 2× $SO_3^-$ | oxycarbonyl halogenide | amine |
| 2 | | 9-methylfluorene | 3× $SO_3^-$ | oxycarbonyl halogenide | amine |
| 3 | | 9-methylfluorene | 4× $SO_3^-$ | oxycarbonyl halogenide | amine |
| 4 | | 9-methylfluorene | 2× $SO_3^-$ | Oxyma ester | amine |

TABLE 1-continued

| # | Protective agent | Backbone | H₂O solubility enhancing group | reactive group | Protected group |
|---|---|---|---|---|---|
| 5 | | 9-methyl-fluorene | 2× $SO_3^-$ | Oxyma B ester | amine |
| 6 | | 9-methyl-fluorene | 2× $SO_3^-$ | oxycarbonyl O-succinimide | amine |
| 7 | | 9-methyl-fluorene | 2× $SO_3^-$ | oxycarbonyl halogenide | amine |
| 8 | | 9-methyl-fluorene | 2× $N(CH_3)_2$ | oxycarbonyl halogenide | amine |
| 9 | | 9-methyl-fluorene | 2× $N(CH_3)_3^+$ | oxycarbonyl halogenide | amine |

TABLE 1-continued

| # | Protective agent | Backbone | H2O solubility enhancing group | reactive group | Protected group |
|---|---|---|---|---|---|
| 10 | 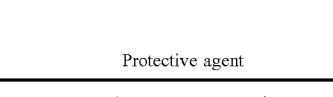 | 9-methyl-fluorene | $N(CH_3)_3^+$ CN | oxycarbonyl halogenide | amine |

Preferred protective agents having the t-butane backbone structure of the present invention can be illustrated by the following general formula 2:

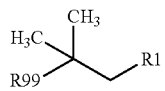

General Formula 2 wherein R1 is selected from $SO_3^-$, $PO_3^{2-}$, $N(CH_3)_2$, $N(CH_3)_3^+$, $OSO_3^-$ ester, $OPO_3^{2-}$ ester and CN. In preferred embodiments R1 is $SO_3^-$. R99 is preferably selected from the group consisting of oxycarbonyl halogenide, oxycarbonyl O-succinimide, oxycarbonyl anhydride, halogenide, oxymethyl halogenide, hydroxide and thiol groups, wherein R99 is more preferably selected from hydroxide, halogenide, thiol, oxycarbonyl O-succinimide and oxycarbonyl anhydride.

Preferred protective agents having the t-butane backbone structure of the present invention are shown in the following table 2. The compounds listed in the table are in no way limiting the scope of the present invention. They constitute illustrative and preferable protective agents according to this invention.

TABLE 2

| # | Protective agent | Backbone | H2O solubility enhancing group | reactive group | Protected group |
|---|---|---|---|---|---|
| 11 | (structure with $H_3C$, $CH_3$, HO, $SO_2O^-$) | t-butane | $SO_3^-$ | hydroxide | carboxyl |
| 12 | (structure with $H_3C$, $CH_3$, HS, $SO_2O^-$) | t-butane | $SO_3^-$ | thiol | thiol |
| 13 | (structure with $H_3C$, $CH_3$, Br, $SO_2O^-$) | t-butane | $SO_3^-$ | bromide | alcohol carboxyl phosphono |
| 14 | (structure with $CH_3$, $CH_3$, Br, $N(CH_3)_2$) | t-butane | $N(CH_3)_2$ | bromide | alcohol carboxyl phosphono |
| 15 | (structure with $CH_3$, $CH_3$, Br, $N^+(CH_3)_3$) | t-butane | $N(CH_3)_3^+$ | bromide | alcohol carboxyl phosphono |

TABLE 2-continued

| # | Protective agent | Backbone | H₂O solubility enhancing group | reactive group | Protected group |
|---|---|---|---|---|---|
| 16 | 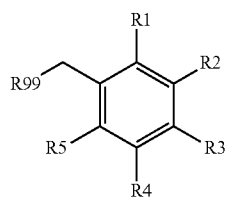 | t-butane | $SO_3^-$ | Oxycarbonyl O-succinimide | amine |

Preferred protective agents having the mono-, di or triphenylmethane backbone structure of the present invention can be illustrated by the following general formula 3, 4 or 5, respectively:

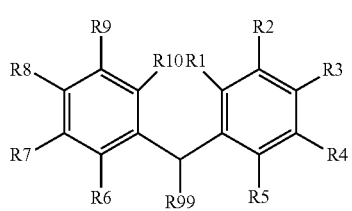

General Formula 3 wherein R1 to R5 are independently selected from hydrogen, $SO_3^-$, $PO_3^{2-}$, $N(CH_3)_2$, $N(CH_3)_3^+$, $OSO_3^-$ ester, $OPO_3^{2-}$ ester and CN with the proviso that at least one, preferably at least two of R1 to R5 are selected from $SO_3^-$, $PO_3^{2-}$, $N(CH_3)_2$, $N(CH_3)_3^+$, $OSO_3^-$ ester, $OPO_3^{2-}$ ester and CN. In preferred embodiments all of R1 to R5 that are not $SO_3^-$, $PO_3^{2-}$, $N(CH_3)_2$, $N(CH_3)_3^+$, $OSO_3^-$ ester, $OPO_3^{2-}$ ester or CN are hydrogen.

R99 is preferably selected from the group consisting of oxycarbonyl halogenide, oxycarbonyl Oxyma ester, oxycarbonyl O-succinimide, oxycarbonyl anhydride, halogenide, oxymethyl halogenide, hydroxide and thiol groups, wherein R99 is more preferably selected from halogenide, oxymethyl halogenide and oxycarbonyl halogenide.

In preferred embodiments R3 is selected from $SO_3^-$, $PO_3^{2-}$, $N(CH_3)_2$, $N(CH_3)_3^+$, $OSO_3^-$ ester, $OPO_3^{2-}$ ester and CN, in particular R3 is $SO_3^-$. Preferably, R1, R2, R4 and R5 are hydrogen.

General Formula 4 wherein R1 to R10 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R10 are selected from $SO_3^-$, $PO_3^{2-}$, $OSO_3^-$ ester, $OPO_3^{2-}$ ester, $N(CH_3)_2$, $N(CH_3)_3^+$, and CN. In preferred embodiments all of R1 to R10 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

R99 is preferably selected from the group consisting of oxycarbonyl halogenide, oxycarbonyl Oxyma ester, oxycarbonyl O-succinimide, oxycarbonyl anhydride, halogenide, oxymethyl halogenide, hydroxide and thiol groups, wherein R99 is more preferably selected from halogenide, oxymethyl halogenide and oxycarbonyl halogenide.

In preferred embodiments R3 and R8 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R8 are selected from $SO_3^-$. Preferably, R1, R2, R4 to R7, R9 and R10 are hydrogen.

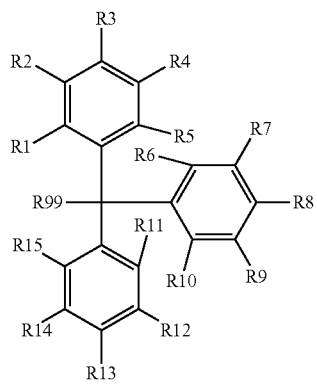

General Formula 5 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

R99 is preferably selected from the group consisting of oxycarbonyl halogenide, oxycarbonyl Oxyma ester, oxycarbonyl O-succinimide, oxycarbonyl anhydride, halogenide, oxymethyl halogenide, hydroxide and thiol groups, wherein R99 is more preferably selected from halogenide, oxymethyl halogenide and oxycarbonyl halogenide. In a particularly preferred embodiment R99 is not halogenide, when R3, R8 and R13 are $SO_3^-$. In another particularly preferred embodiment R99 is not chloride, when R3, R8 and R13 are $SO_3^-$. In a preferred embodiment R99 is preferably selected from the group consisting of oxycarbonyl halogenide, oxycarbonyl Oxyma ester, oxycarbonyl O-succinimide, oxycarbonyl anhydride, oxymethyl halogenide, hydroxide and thiol groups. In particularly preferred embodiment R99 is not halogenide, particularly not chloride.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$.

Preferably, R1, R2, R4 to R7, R9 to R12, R14 and R15 are hydrogen.

Preferred protective agents having the mono-, di or tri-phenylmethane backbone structure of the present invention are shown in the following table 3. The compounds listed in the table are in no way limiting the scope of the present invention. They constitute illustrative and preferable protective agents according to this invention.

TABLE 3

| # | Protective agent | Backbone | H2O solubility enhancing group | reactive group | Protected group |
|---|---|---|---|---|---|
| 17 | | phenyl-methane | $SO_3^-$ | oxycarbonyl-halogenide | amine |
| 18 | | phenyl-methane | $SO_3^-$ | halogenide | alcohol carboxyl seleno phosphono |
| 19 | | phenyl-methane | $N(CH_3)_2$ | halogenide | alcohol carboxyl seleno phosphono |
| 20 | | phenyl-methane | $N(CH_3)_3^+$ | halogenide | alcohol carboxyl seleno phosphono |
| 21 | | phenyl-methane | $SO_3^-$ | oxymethyl-halogenide- | alcohol |
| 22 | | diphenyl-methane | 2× $SO_3^-$ | oxycarbonyl-halogenide | amine |

TABLE 3-continued

| # | Protective agent | Backbone | H2O solubility enhancing group | reactive group | Protected group |
|---|---|---|---|---|---|
| 23 | 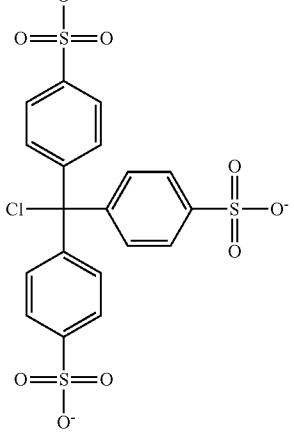 | triphenyl-methane | 3× $SO_3^-$ | halogenide | alcohol |

Preferably, the functional group is present on an amino acid, peptide or protein and the chemical reaction is peptide or protein synthesis in a solvent as mentioned above and below.

The protective agents as mentioned above and below provide a protecting group to the amino acids or peptides. In preferred embodiments, the α-amine protecting group is at least one of the following formulas 6 to 10. In each case the nitrogen shown in the following general formula belongs to the protected amino group:

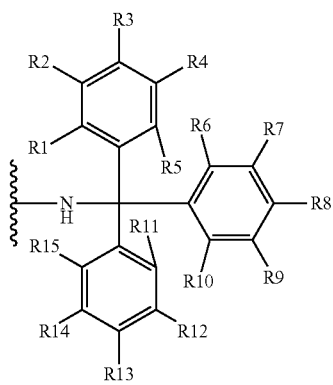

General Formula 6 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $N(CH_3)_2$, $OSO_3^-$ ester, $OPO_3^{2-}$ ester, $N(CH_3)_3^+$ or CN. In preferred embodiments all of R1 to R15 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

In preferred embodiments R3, R8 and R13 are selected from $SO_3^-$, $PO_3^{2-}$, $OSO_3^-$ ester, $OPO_3^{2-}$ ester, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

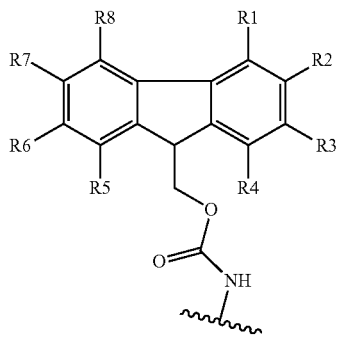

General Formula 7 wherein R1 to R8 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R8 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R8 that are not $SO_3^-$, $PO_3^{2-}$, $N(CH_3)_2$, $N(CH_3)_3^+$, $OSO_3^-$ ester, $OPO_3^{2-}$ ester or CN are hydrogen.

In preferred embodiments R2 and R7 are selected from $SO_3^-$, $OSO_3^-$ ester, $OPO_3^{2-}$ ester, $PO_3^{2-}$, $N(CH_3)_2$, $N(CH_3)_3^+$ and CN, in particular R2 and R7 are $SO_3^-$. Preferably, R1, R3 to R6 and R8 are hydrogen.

In preferred embodiments R3 and R6 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R6 are $SO_3^-$. Preferably, R1, R2, R4, R5, R7 and R8 are hydrogen.

In preferred embodiments R2 and R6 are selected from $SO_3^-$, $PO_3^{2-}$, $OSO_3^-$ ester, $OPO_3^{2-}$ ester, $N(CH_3)_2$, $N(CH_3)_3^+$ and CN, in particular R2 and R6 are $SO_3^-$. Preferably, R1, R3, R4, R5, R7 and R8 are hydrogen.

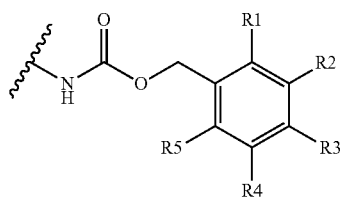

General Formula 8 wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R5 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

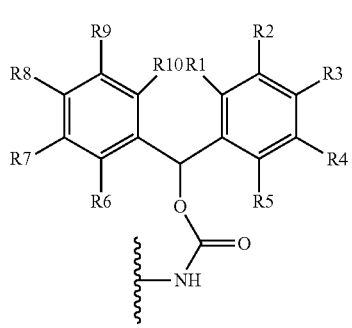

General Formula 9 wherein R1 to R10 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R10 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R10 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 and R8 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R8 are selected from $SO_3^-$. Preferably, R1, R2, R4 to R7, R9 and R10 are hydrogen.

General Formula 10

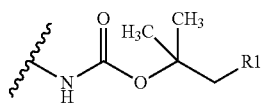

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

In particularly preferred embodiments the α-amine protecting group is a 9-(2-sulfo)fluorenylmethyloxycarbonyl group (Sulfmoc), 9-(3,6-disulfo)fluorenylmethyloxy-carbonyl group, 9-(2,7-disulfo)fluorenylmethyloxy-carbonyl group or a tert-butyl-(2-sulfonate)oxycarbonyl group (Sboc). As used herein, the term "Smoc" denotes a 9-(3,6-disulfo)fluorenylmethyloxy-carbonyl group or a 9-(2,7-disulfo)fluorenylmethyloxy-carbonyl group.

In a preferred embodiment of the invention, any reactive side chain functional group of said first amino acid or first peptide and/or said second amino acid or second peptide is protected with a side chain protecting group, which preferably comprises at least one water solubility enhancing functional group. The side chain protecting group may comprise a sulfonic group or a sulfonic ester. The method preferably comprises the step of removing the side chain protecting groups. The water solubility enhancing functional group of the side chain protecting group provides solubility to the side chain protected amino acid or peptide. Suitable side chain protecting groups are the reaction products of one of the protective agents mentioned above with the respective side chain functional group of the amino acid or peptide.

Regarding the side chain protecting groups, preferred amine protecting groups are those shown in the following formulae 11 to 15, wherein the nitrogen belongs to the protected amino group.

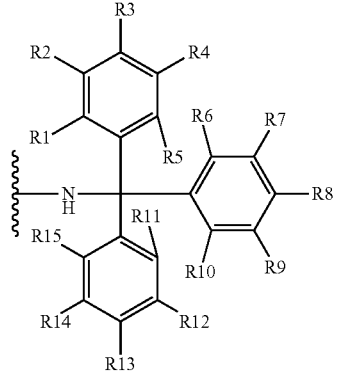

General Formula 11 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

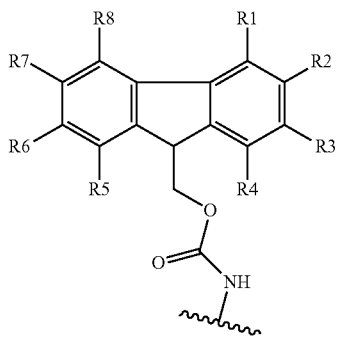

General Formula 12

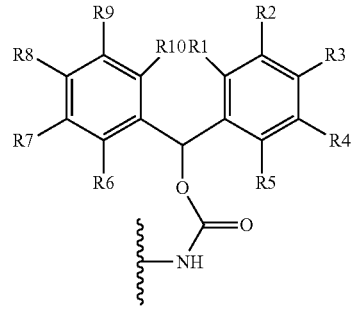

General Formula 14 wherein R1 to R8 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R8 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R8 that are not $SO_3^-$, $PO_3^{2-}$ $OSO_3^-$ ester, $OPO_3^{2-}$ ester, $N(CH_3)_2$, $N(CH_3)_3^+$ or CN are hydrogen.

In preferred embodiments R2 and R7 are selected from $SO_3^-$, $OSO_3^-$ ester, $OPO_3^{2-}$ ester, $PO_3^{2-}$, $N(CH_3)_2$, $N(CH_3)_3^+$ and CN, in particular R2 and R7 are $SO_3^-$. Preferably, R1, R3 to R6 and R8 are hydrogen.

In preferred embodiments R3 and R6 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R6 are $SO_3^-$. Preferably, R1, R2, R4, R5, R7 and R8 are hydrogen.

In preferred embodiments R2 and R6 are selected from $SO_3^-$, $PO_3^{2-}$, $OSO_3^-$ ester, $OPO_3^{2-}$ ester, $N(CH_3)_2$, $N(CH_3)_3^+$ and CN, in particular R2 and R6 are $SO_3^-$. Preferably, R1, R3, R4, R5, R7 and R8 are hydrogen.

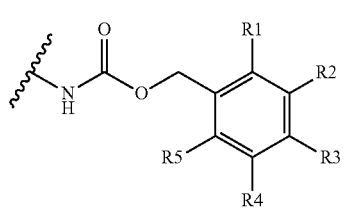

General Formula 13 wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

wherein R1 to R10 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R10 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R10 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 and R8 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R8 are selected from $SO_3^-$. Preferably, R1, R2, R4 to R7, R9 and R10 are hydrogen.

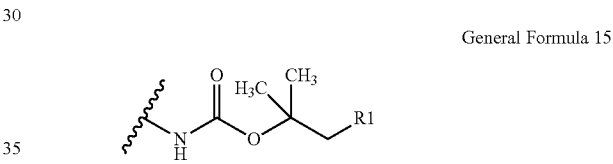

General Formula 15 wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

In particularly preferred embodiments, the side chain amine protecting group is selected from 9-(2-sulfo)fluorenylmethyloxycarbonyl group (Sulfmoc), 9-(3,6-disulfo)fluorenylmethyloxy-carbonyl group, 9-(2,7-disulfo)fluorenylmethyloxy-carbonyl group, tri(4-sulfophenyl)methyl group (SulfoTrt), tert-butyl-(2-sulfonate)oxycarbonyl group (Sboc) and 4-sulfo-carbobenzyloxy group (SulfoCBz).

Preferred alcohol protecting groups are shown in the following formulae 16 to 19. In each case the oxygen shown in the following general formula belongs to the protected alcohol group:

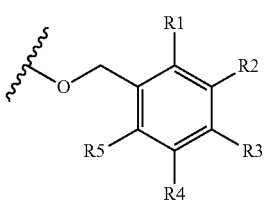

General Formula 16 wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

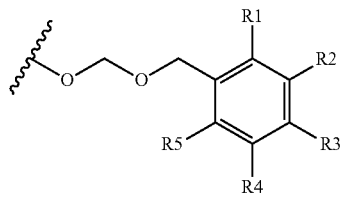

General Formula 17 wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

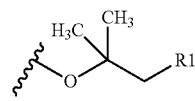

General Formula 18 wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

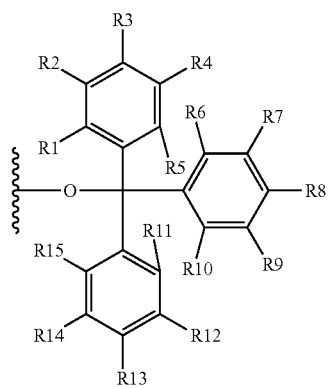

General Formula 19 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $PO_3^{2-}$, $OSO_3^-$ ester, $OPO_3^{2-}$ ester, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

In particularly preferred embodiments the alcohol protecting groups are selected from 4-sulfobenzyl group (BzS), 4-sulfo-benzyloxymethyl group (BOMS), tri(4-sulfophenyl)methyl group (SulfoTrt) and tert-butyl-1-sulfonate group (tBuS).

Preferred thiol protecting groups are shown in the following formulae 20 and 21. In each case the sulfur shown in the following general formula belongs to the protected thiol group:

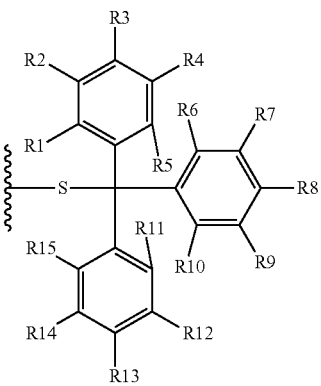

General Formula 20 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

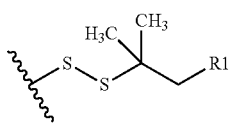

General Formula 21 wherein R1 is selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments R1 is $SO_3^-$.

In particularly preferred embodiments the thiol protecting group is selected from tri(4-sulfophenyl)methyl group (SulfoTrt) and 1-sulfo-2-methyl-2-propanethiol group (StBuS).

Preferred carboxyl protecting groups are those shown in the following formulae 22 to 25. In each case the oxygen shown in the following general formula belongs to the protected carboxyl group:

General Formula 22

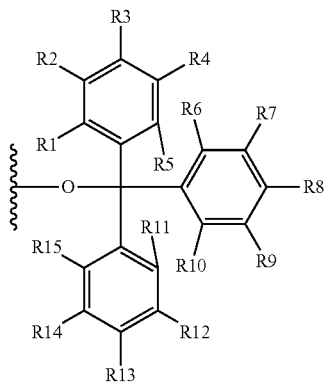

wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

General Formula 23

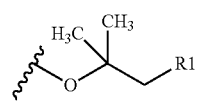

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

General Formula 24

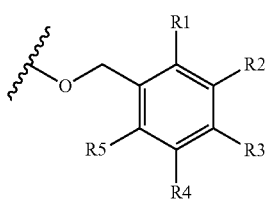

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ and CN, in particular R3 is $SO_3^-$. Preferably, R1, R2, R4 and R5 are hydrogen.

General Formula 25

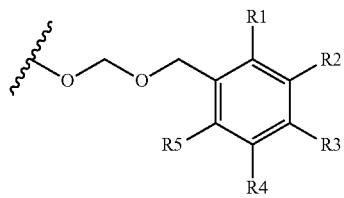

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ and CN, in particular R3 is $SO_3^-$. Preferably, R1, R2, R4 and R5 are hydrogen.

In particularly preferred embodiments the carboxyl protecting groups are selected from 4-sulfobenzyl group (BzS), 4-sulfo-benzyloxymethyl group (BOMS), tri(4-sulfophenyl)methyl (SulfoTrt) group and tert-butyl-1-sulfonate group (tBuS).

Preferred seleno protecting groups are those shown in the following formula 26. In each case the selenium shown in the following general formula belongs to the protected seleno group:

General Formula 26

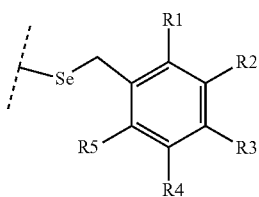

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ or CN, in particular R3 is $SO_3^-$. Preferably, R1, R2, R4 and R5 are hydrogen.

Preferred phosphono protecting groups are those shown in the following formulae 27 and 28. In each case the oxygen shown in the following general formula belongs to the protected phosphono group:

General Formula 27

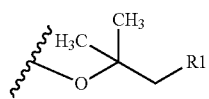

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

General Formula 28

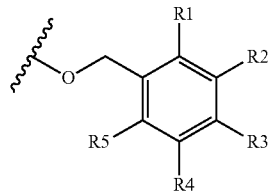

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ and CN, in particular R3 is $SO_3^-$. Preferably, R1, R2, R4 and R5 are hydrogen.

The following is an overview over the most preferred protecting groups.

Amine Protecting Groups

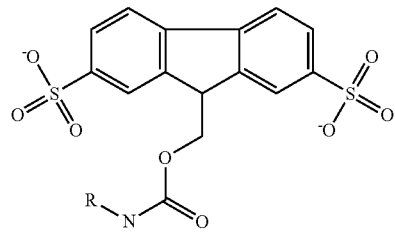

Smoc

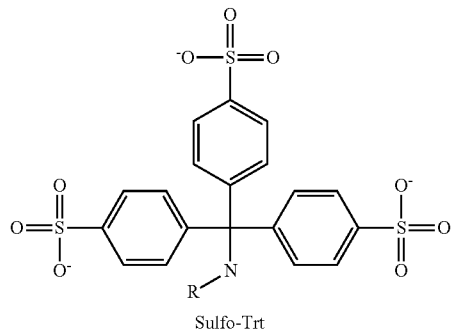

Sulfo-Trt

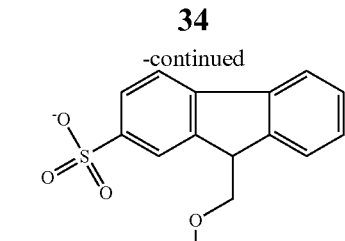

Sulfmoc

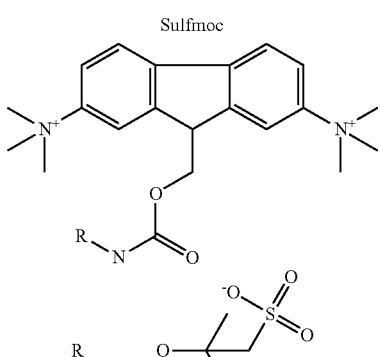

Sboc

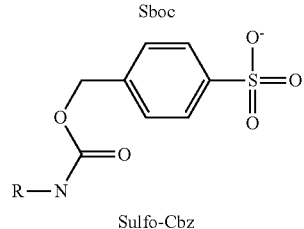

Sulfo-Cbz

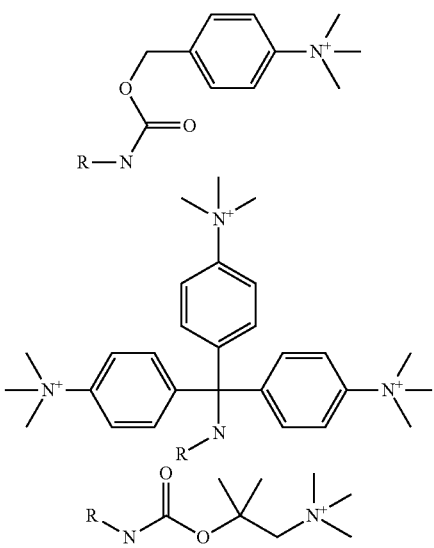

Alcohol Protecting Groups

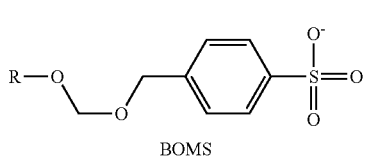

BOMS

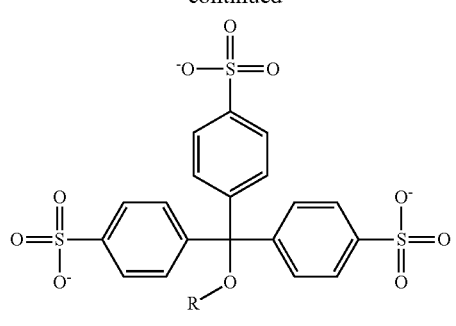
Sulfo-Trt
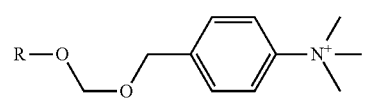
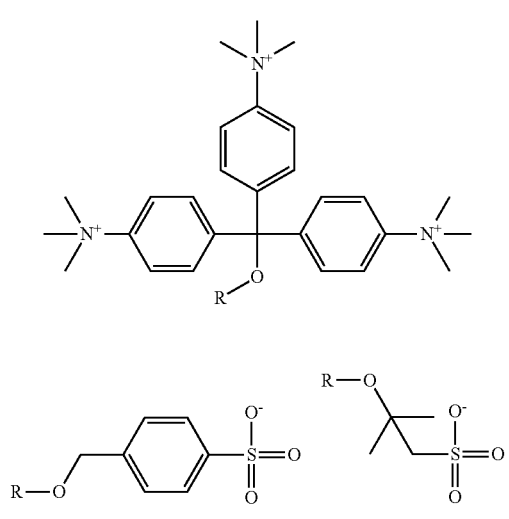
BzS  tBuS
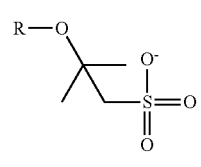
Thiol Protecting Groups
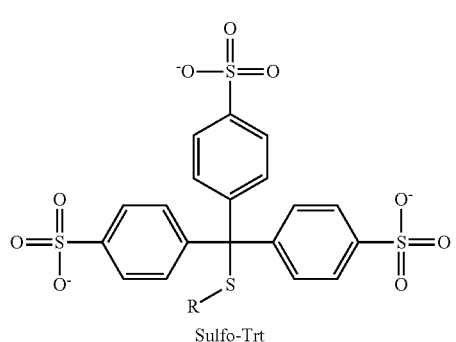
Sulfo-Trt
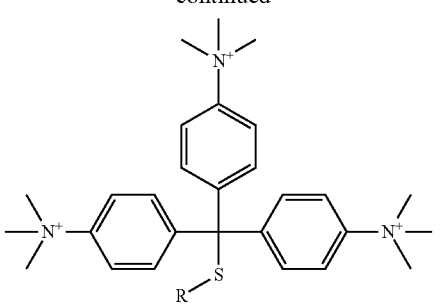
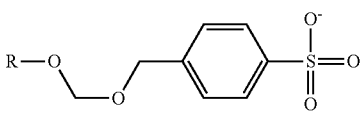
StBuS
Carboxyl Protecting Groups
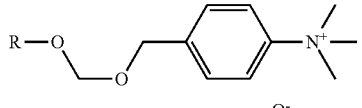
BOMS
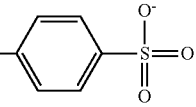
BzS
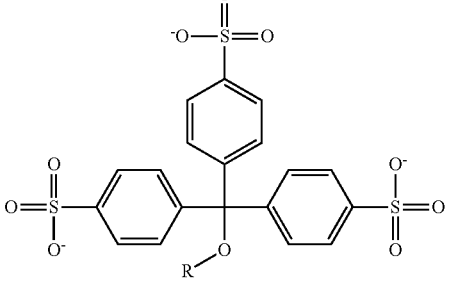
Sulfo-Trt
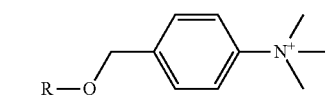
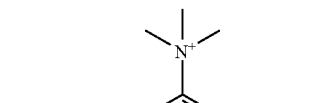
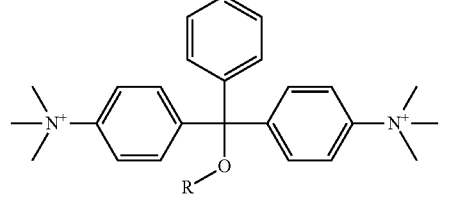

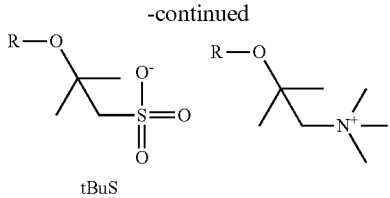

tBuS

Phosphono Protecting Groups

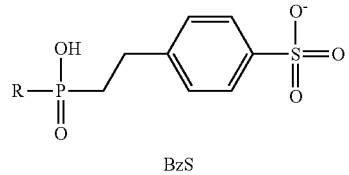

BzS

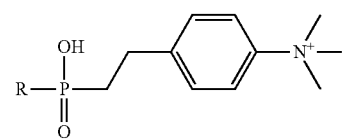

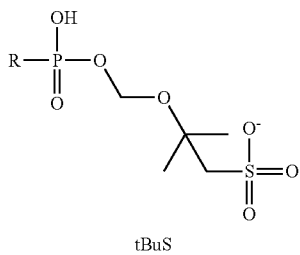

tBuS

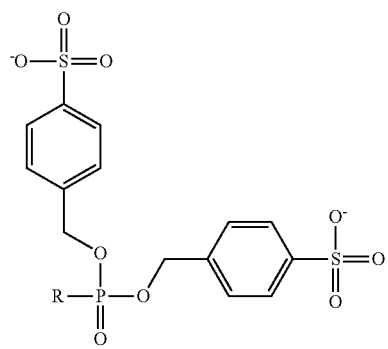

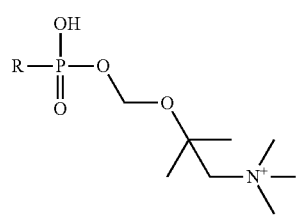

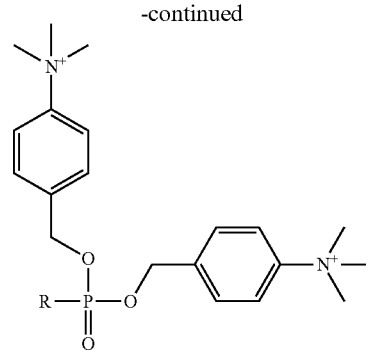

Preferably, the amino protecting groups mentioned above are used to protect the main chain amino group and to provide an anchoring point to the amino acid or peptide to the solid phase, if an ion exchanger is used.

In a specific embodiment, said protecting group having a water-solubility enhancing group preferably comprises at least two water-solubility enhancing groups, preferably ionic groups. This embodiment provides the advantage that a higher bonding to an ion exchanger can be achieved.

In another embodiment, said protecting group having a water-solubility enhancing group preferably comprises exactly one water-solubility enhancing group, preferably ionic group. This embodiment provides the advantage that a lower hydrolyzation of protecting groups can be achieved such that a reaction in water or other protic solvent provides higher yield.

Preferably, said protecting group having a water-solubility enhancing group comprises a fluorenylmethoxycarbonyl residue (Fmoc) being modified with a water-solubility enhancing group, preferably ionic group.

According to an embodiment of the invention, it is preferably provided that any reactive side chain functional group of said amino acid or peptide, preferably first amino acid or first peptide and/or said second amino acid or second peptide, is protected with a side chain protecting group. Astonishing improvements regarding to solubility of the first amino acid or first peptide and/or said second amino acid or second peptide can be achieved by that embodiment. In addition thereto, the binding of first amino acid or first peptide to an ion exchanger is preferably improved.

In a specific embodiment, said side chain protecting group comprises at least one water solubility enhancing functional group, preferably ionic group.

In another embodiment, said side chain protecting group does not comprise any water solubility enhancing functional group.

In methods according to the invention, it can also be provided that the functional group of said first amino acid or first peptide and said second amino acid or second peptide being protected is selected from α-amino, side chain amino, thiol, carboxyl, hydroxyl, phosphono and seleno.

In a preferred embodiment of the present invention the second amino acid or second peptide does not comprise preferably any protecting groups with the exception of groups protecting a primary amine group and with the exception of groups protecting a carboxylic group. More preferably, the second amino acid or second peptide does not preferably comprise any protecting groups with the exception of groups protecting a primary amine group. This embodiment provides astonishing cost improvements and an easier processing. With regard to achieve a higher solubility of the amino acid being coupled to a growing peptide chain a protecting group might be used in some cases.

Furthermore, the solubility of the second amino acid or second peptide is preferably improved by the use of a salt of the second amino acid or second peptide and the salt comprises a soluble organic ion such as quaternary amino cations. Furthermore, compounds imparting solubility to salts in organic solvents are preferably applied, such as crown ethers. Additionally, the second amino acid or second peptide can be added to the reaction mixture in solid phase and a transport of the added second amino acid or second peptide to the first amino acid or first peptide is achieved via the solvent. This embodiment comprises cost advantages. However, the reaction time is longer than in other embodiments.

The solubility of the second amino acid or second peptide is preferably sufficient for achieving an adequate concentration of the second amino acid or second peptide in the mixture added to the activated first amino acid or first peptide and/or the growing chain being obtained. As mentioned above, the solubility of the second amino acid or second peptide can be improved if useful. However, in many cases there is no need to improve the solubility of the second amino acid or second peptide.

Preferably, the following amino acids are used without any protection group as the second amino acid or second peptide Alanine (Ala), Glycine (Gly), Isoleucine (Ile), Leucine (Leu), Proline (Pro), Valine (Val), Phenylalanine (Phe), Arginine (Arg), Asparagine (Asn), Glutamine (Gln), Tyrosine (Tyr), Tryptophan (Trp), Histidine (His), Methionine (Met), more preferably Ala, Gly, Ile, Leu, Pro, Val, Phe. These amino acids have conventionally a sufficient solubility for achieving an adequate concentration of the second amino acid or second peptide in the mixture added to the activated first amino acid or first peptide and/or the growing chain being obtained.

The amino acids Glutamic acid (Glu), Aspartic acid (Asp), Cysteine (Cys), Lysine (Lys), Serine (Ser), Threonine (Thr) comprise preferably a protection group, more preferably a side chain protection group as mentioned above and below.

Preferably, said amino acid or peptide comprising a protecting group having a water-solubility enhancing group is added to said ion exchanger in an amount of at least 10%, more preferably at least 80% of the capacity of the ion exchanger.

Preferably, said amino acid or peptide being bound to a solid phase is added to said solid phase in an amount of at least 10%, more preferably at least 80% of the capacity of the solid phase.

According to the invention, it is preferably provided that said forming of the peptide bond is achieved using a solution of second amino acid or peptide wherein the concentration of the second amino acid or the second peptide is in the range of 0.01 to 90% by weight, preferably in the range of 0.1 to 50% by weight, more preferably in the range of 0.5 to 20% by weight based on the total weight of the solution.

In an embodiment of the present invention, forming of the peptide bond is preferably achieved at a temperature in the range of −20 to 100° C., more preferably 0 to 50° C., even more preferably 10 to 30° C.

In a further embodiment of the present invention, forming of the peptide bond is preferably achieved at a pH value in the range of 4 to 12, preferably in the range of 6 to 10, more preferably in the range of 7 to 9.5, even more preferably in the range of 7 to 9.0 and even more preferably in the range of 7 to 8.5.

According to the invention, it is preferably provided that the peptide being obtained by forming of the peptide bond comprises 2 to 150 amino acid units, more preferably 2 to 6 amino acid units, even more preferably 2 to 4 amino acid units.

According to a further embodiment of the present invention, it is preferably provided that the peptide being obtained by forming of the peptide bond comprises 4 to 300 amino acid units, more preferably 10 to 100 amino acid units, even more preferably 15 to 45 amino acid units. Peptides having a high number of amino acid units are preferably achieved by a method wherein a first amino acid or first peptide is covalently bound to a solid phase.

As mentioned above and below some of the embodiments of the present invention include a deprotection step. Conventionally, a deprotection solution is applied in order to achieve a deprotection of the peptide or a specific amino acid unit of the peptide.

The deprotecting solutions that are suitable for use in the present invention preferably comprise an acid or base, preferably an aqueous acid or base, i.e. the acid and/or base preferably is water-soluble. Preferred acids are phosphoric acid, hydrochloric acid or trifluoro acetic acid. Preferred bases are amines and ammonia. Preferred deprotecting solutions are amine and/or ammonia solutions. The base is used in an amount and to the extent necessary to deprotect the functional group. The solubility of certain organic bases may limit the amount that can be dissolved in the water, alcohol or mixture of water and alcohol. Suitable bases are those having a solubility that allows for dissolving a sufficient amount to carry out the deprotection in the selected solvent.

The deprotecting solution for deprotecting a Sboc group preferably comprises an aqueous acid, such as phosphoric acid, hydrochloric acid or trifluoro acetic acid.

The deprotecting solution for deprotecting a Smoc group, a Sulfmoc group and/or similar groups such as fluorenylmethyloxy-carbonyl groups being derived from compounds or groups of formulae 1, 7, 12 etc. preferably comprises a water soluble base such as amine, ammonia or inorganic hydroxides. The water soluble base is used in an amount and to the extent necessary to deprotect the peptide. The solubility of certain organic bases may limit the amount that can be dissolved in the water, alcohol or mixture of water and alcohol. Suitable bases are those having a solubility that allows for dissolving a sufficient amount to carry out the deprotection in the selected solvent.

Surprising improvements for deprotecting a Smoc group, a Sulfmoc group and/or similar groups can be achieved by using at least 5% of an organic base, such as primary, secondary and/or tertiary amines, preferably, piperazine, piperidine, ethanolamine and/or ethylendiamine in water or mixtures of water and environmentally friendly solvents including protic solvents, such as water, primary, secondary and/or tertiary alcohols, non-protic solvents such as ketones, nitriles, lactones, lactams, carbon acid amides, carbon acid ester, ether, urea derivatives, sulfoxides, sulfones, carbonate ester. Preferred examples of non-protic solvents are e. g. dimethylacetamide, ethyl methyl ketone, acetone, methyl isopropyl ketone, methyl isobutyl ketone, methyl n-butyl ketone, methyl t-butyl ketone, methyl isoamyl ketone, dimethyl sulfoxide, hexamethylphosphoric triamide, tetrahydrofuran, dioxane, dimethoxyethane, diethylene glycol, dimethyl ether, ethyl acetate, tertiary butyl acetate, or mixture(s) thereof. This reduces base catalysed side reactions (e.g. the deprotection of OtBu based side chain protecting groups, cleavage of esters with SPPS linker molecules) during deprotection of the Smoc group, the Sulfmoc group and/or similar groups compared to the usage of ammonia or inorganic hydroxides. This results in a higher purity and product yield.

It will be understood that after deprotection, the reaction and deprotection steps can be repeated using further amino acids or further peptides wherein the α-amino group or the carboxylic group of said further amino acid and/or further peptide is preferably protected with a protecting group according to this invention, in particular an Smoc group or an Sboc group, until the desired target peptide is obtained.

In an embodiment, the method further comprises the step of releasing the resulting peptide from the polymeric support with a releasing composition when the peptide is complete.

In the case that the peptide is ionically bound to an ion exchanger by a protecting group having a water-solubility enhancing group, the releasing composition is preferably a composition deprotecting the peptide from the corresponding protecting group or a composition being able to release the peptide from the ion exchanger and maintaining the protection of the peptide. The deprotecting agent being used for releasing the peptide from the solid support depends on the protecting group being used. A Sboc group is conventionally released by an acidic composition while basic reagents are used to remove the Smoc moiety.

In a specific embodiment of the present invention, the forming a peptide bond is preferably achieved while an amino acid or a peptide is ionically bound to an ion exchanger and after forming the peptide bond the obtained peptide is removed from the ion exchanger by deprotecting the obtained peptide. In preferred embodiments at least one preferably at least 50% and more preferably at least 90% of side chain protecting groups that are attached to the amino acids in the target peptide are removed by the releasing composition.

In another embodiment of the present invention, the forming a peptide bond is preferably achieved while an amino acid or a peptide is ionically bound to an ion exchanger and after forming the peptide bond the obtained peptide is removed from the ion exchanger by adding a ionic solution and maintaining the protection of the obtained peptide.

Preferably, release is carried out in the presence of scavenger compositions (e.g. water, phenol, DTT, triethylsilane and anisole), which protect the peptide from undesired side reactions during and after the cleaving step. A skilled person can select a suitable scavenger with regard to the protecting groups that are present.

The released peptide can be separated from the ion exchanger by filtration and the peptide can then be recovered from the filtrate by a conventional step such as evaporation or solvent-driven precipitation.

In the case that the peptide is covalently bound to a solid support, an appropriate cleaving composition is preferably used. Suitable cleaving compositions and methods are well known to a skilled person. Typically, an acid, such as trifluoroacetic acid and hydrofluoric acid (HF), is used to carry out the cleaving step. Preferably, an acid suitable for cleaving the desired peptide from the polymeric support concurrently removes side chain protecting groups that are attached to the amino acids in the target peptide.

Preferably, cleavage or release is carried out in the presence of scavenger compositions (e.g. water, phenol, DTT, triethylsilane and anisole), which protect the peptide from undesired side reactions during and after the cleaving step. A skilled person can select a suitable scavenger with regard to the protecting groups that are present.

The cleaved or released peptide can be separated from the cleaved support (e.g. a resin) by filtration and the peptide can then be recovered from the filtrate by a conventional step such as evaporation or solvent-driven precipitation.

In another preferred embodiment of the invention, the method further comprises at least one washing step using a solvent comprising a protic and/or non-protic solvent as mentioned above and below regarding the forming of the peptide bond, and a step of collecting waste solutions obtained in the washing steps, contacting the waste solutions to an affinity chromatography column, preferably a solid anion and/or cation exchange support, thereby retaining waste compounds that comprise a water-solubility enhancing functional group, particular a charged functional group like $SO_3^-$, $OSO_3^-$ ester, $OPO_3^{2-}$ ester, $PO_3^{2-}$, and $N(CH_3)_3^+$. It has been particularly effective to use an anion exchange support for removal of compounds that contain at least one sulfonic group. Subsequently, the waste compounds may be collected by regeneration of the affinity chromatography column, preferably a solid anion and/or cation exchange support, and disposed. Alternatively, the affinity chromatography column, preferably an anion and/or cation exchange support material, containing the waste compounds may be disposed.

Washing steps are typically carried out after the coupling step and after the deprotection step. The anion and/or cation exchange step allows for the removal of all sulfo-containing compounds, such as unreacted or cleaved protecting groups and reagents, e.g. coupling agents and capping reagents as described herein from the washing solutions. The waste compounds are retained on the anion or cation exchange column and a purified solvent is obtained. The retained compounds can be disposed together with the anion or cation exchange material or after elution and only a minimum amount of chemical waste has to be disposed.

In a further preferred embodiment of the invention, the method further comprises a purification step after the releasing step wherein the solution containing the deprotected and released target protein or peptide is contacted to an affinity chromatography column, preferably a solid anion and/or cation exchange support, thereby retaining waste compounds such as those comprising a sulfonic group, and collecting the purified target protein. In preferred embodiments the waste compounds comprise at least one sulfonic group as part of the protecting groups and other reagents. Due to the sulfo-containing protecting groups, and the sulfo-containing reagents it is possible to remove substantially all of the excess chemicals and side products generated during the coupling, the deprotection and the cleaving reactions in a protic and/or non-protic solvent as mentioned above and below by affinity chromatography column, preferably ion exchange methods. Of course, this also works with the other charged functional groups. Only the target peptide is able to run through the ion exchange column whereas the peptide side products, protecting group residues and excess reagents are retained on the column. After regeneration of the column, only a minimum amount of chemical waste has to be disposed. This is a beneficial effect of using charged functional groups such as $SO_3^-$, $OSO_3^-$ ester, $OPO_3^{2-}$ ester, $PO_3^{2-}$, and $N(CH_3)_3^+$. But even if one or more of the uncharged functional groups are used, the process can still be carried out in water or in another environmentally friendly solvent, thereby reducing the amount of waste chemicals compared to prior art processes.

A further subject matter of the present invention is a peptide obtainable by a method according to the present invention.

A further subject matter of the present invention is an amino acid or a peptide comprising a protecting group having a water-solubility enhancing group being bound to the amino group and an activated or free carboxyl group, preferably an activated carboxyl group. Preferably, the peptide is ionically bound to an ion exchanger.

It is preferably provided that the amino acid or peptide according to the present invention preferably has 1 to 150 amino acid units, preferably 1 to 50 amino acid units, more preferably 1 or 2 amino acid units.

Another aspect of the present invention relates to modified amino acids, peptides and salts thereof comprising a protecting group selected from the group consisting of those shown above under formulae 6 to 25, more preferably selected from those shown above under formulae 6 to 10. In particularly preferred embodiments these protecting groups include 9-(2-sulfo)fluorenylmethyloxycarbonyl group (Sulfmoc), 9-(3,6-disulfo)fluorenylmethyloxy-carbonyl group, 9-(2,7-disulfo)fluorenylmethyloxy-carbonyl group, tri(4-sulfophenyl)methyl group (SulfoTrt), tert-butyl-(2-sulfonate)oxycarbonyl group (Sboc), 4-sulfo-carbobenzyloxy group (SulfoCBz), tert-butyl-1-sulfonate group (tBuS), 1-sulfo-2-methyl-2-propanethiol group (StBuS), 4-sulfobenzyl group (BzS), and 4-sulfo-benzyloxymethyl group (BOMS).

The invention is illustrated but not limited by the following examples.

EXAMPLES

Example 1: Synthesis of 9-(3,6-disulfo)fluorenylmethyloxycarbonyl Chloride (Smoc-Cl)

2 g (7.73 mmol) of Fmoc-chloride was treated with 20 mL of concentrated sulfuric acid. After work up of the reaction mixture 2.96 g (7.07 mmol, 91.4%) of crude Smoc-chloride was obtained in form of a slightly yellow solid.

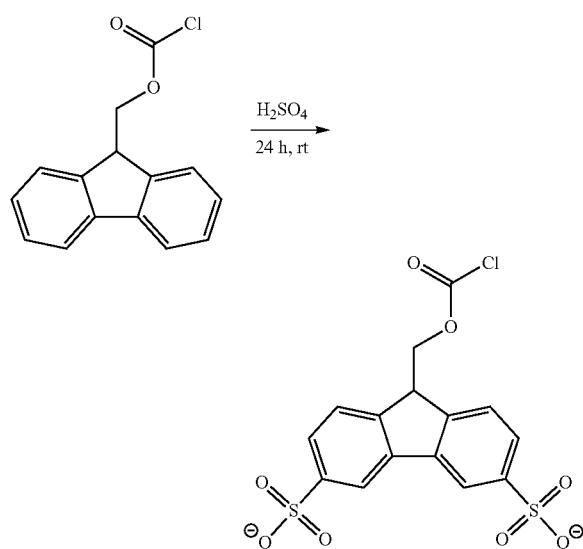

Analytical data of Smoc-chloride: $^1$H NMR (500 MHz, $D_2O$) δ=7.80 (s, 2H), 7.69 (d, J=7.9 Hz, 2H), 7.48 (d, J=7.8 Hz, 2H), 3.84 (d, J=4.8 Hz, 2H), 3.45 (t, J=4.7 Hz, 1H).

$^{13}$C NMR (126 MHz, $D_2O$) δ=145.57, 142.54, 141.65, 125.16, 121.61, 120.90, 62.54, 49.65.

Example 2: Synthesis of 9-(2,7-disulfo)fluorenylmethyloxycarbonyl Chloride (Smoc-Cl)

2 g (7.73 mmol) of Fmoc-chloride were treated with 20 mL of concentrated sulfuric acid and heated to 100° C. Sulfuric acid was neutralised with NaOH (pH 9.5) and solvent removed under reduced pressure and NMR analytics confirmed formation of target intermediate. The intermediate was dissolved again in 20% sulfuric acid in water, stirred for 6 h to form 9-(2,7-disulfo)fluorenylmethanol. Sulfuric acid was neutralised with NaOH (pH 6.7) and the solvent removed under reduced pressure. A solution of 1.2 eq. phosgene in 25 ml of DCM was cooled to 0° C. and 9-(2,7-disulfo)fluorenylmethanol was added slowly under stirring (Carpino and Han, *The Journal of Organic Chemistry* 1972, 37, (22), 3404-3409). The solution was stirred for 1 h in the ice bath and then let stand for 4 h at ice-bath temperature. Solvent and excess phosgene were removed under reduced pressure giving the corresponding product.

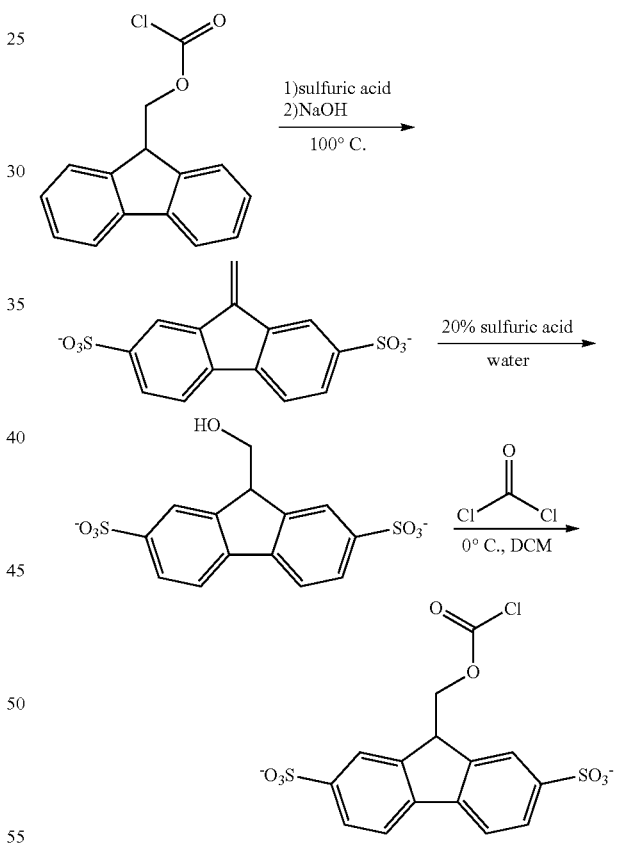

NMR Intermediate:

$^1$H NMR (300 MHz, $D_2O$) δ: 6.09 (s, 2H), 7.23-7.40 (m, 2H), 7.72 (s, 2H), 7.95 (d, J=6.2 Hz, 2H).

$^{13}$C NMR (75 MHz, $D_2O$) δ: 142.61, 132.99, 131.74, 130.23, 129.28, 127.22, 125.57, 124.69.

LC-APCI-MS for 9-(2,7-disulfo)-fluorenylmethyloxycarbonyl chloride:

LC-APCI-MS calculated for $C_{15}H_9ClO_{22}$·m/z: 256.03. Measured m/z: 256.94 [M-H—2×$SO_3$]$^-$.

Example 3: Synthesis of Smoc-ßAla-OH (Smoc-ß-alanine)

8.41 mmol of Fmoc-ß-alanine were treated with 30 mL of concentrated sulfuric acid. After work up of the reaction mixture 8.09 mmol (96.2%) of crude Smoc-ß-alanine were obtained.

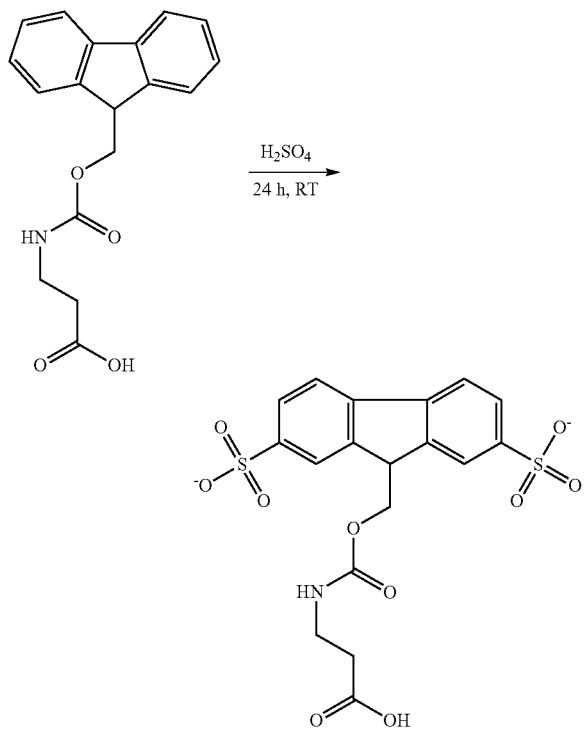

Example 4: Synthesis of L-carnosine

Smoc-ß-alanine is added to an ion exchange resin (DEAE Sephadex A-25; GE Healthcare) at a maximum load. Smoc-ß-alanine is activated by 3 equivalents 1-ethyl-3-(3-dimethylaminopropyl)carbodiimid (EDC) and 2 equivalents N-hydroxysuccinimide (NHS) in water.

Thereafter, the ion exchanger loaded with the activated Smoc-ß-alanine is washed two times with water. After the washing steps, 1.5 equivalents L-histidine solved in water are added to the activated Smoc-ß-alanine and reacted at 4° C. for 12 minutes at pH 7.5 under agitation. Excess of L-histidine and released NHS are removed by washing with water.

The formed L-carnosine is released by deprotection using 0.25 mM NaOH (pH 10, 20 minutes) or $Na_2CO_3$ (pH 10, 20 minutes).

Example 5: Synthesis of L-carnosine

Smoc-ß-alanine is added to an ion exchange resin (DEAE Sephadex A-25; GE Healthcare) at a maximum load. Smoc-proline is obtained in a similar manner as disclosed above with regard to Smoc-ß-alanine (see Example 3). Smoc-ß-alanine is activated by 3 equivalent 1-ethyl-3-(3-dimethylaminopropyl)carbodiimid (EDC) and 2 equivalents N-hydroxysuccinimide (NHS) in mixture of water and acetonitrile (MeCN) 4:1 ratio (volume). The activation was much higher than in example 4.

Thereafter, the ion exchanger loaded with the activated Smoc-ß-alanine is washed two times with water. After the washing step, 1.5 equivalents L-histidine solved in water are added to the activated Smoc-ß-alanine and reacted at 4° C. for 12 minutes at pH 7.5 under agitation. Excess of L-histidine and released NHS are removed by washing with water.

The yield in example 5 is higher than the yield in example 4.

The formed L-carnosine is released by deprotection using 0.25 M NaOH (pH 10, 10 minutes) or $Na_2CO_3$ (pH 10, 20 minutes).

Example 6: Synthesis of Pro-Tyr-OMe

Smoc-proline is added to an ion exchange resin (DEAE Sephadex A-25; GE Healthcare) at a maximum load. Smoc-proline is activated by 3 equivalents 1-ethyl-3-(3-dimethylaminopropyl)carbodiimide (EDC) and 2 equivalents N-hydroxysuccinimide (NHS) in mixture of water and tetrahydrofuran (THF) 3:1 ratio (volume).

Thereafter the ion exchanger loaded with the activated Smoc-proline is washed two times with water. After the washing step, 1.5 equivalents L-tyrosine methyl ester solved in water are added to the activated Smoc-proline and reacted at 24° C. for 12 minutes at pH 8 under agitation. Excess of L-tyrosine methyl ester and released NHS are removed by washing with water.

The formed Pro-Tyr-OMe is released by deprotection using 0.5 M NaOH (pH 9, 25 minutes) or $Na_2CO_3$ (pH 10, 20 minutes).

Example 7: Synthesis of Pro-Tyr-OMe

Smoc-proline is added to an ion exchange resin (Amberlite IRA-900; Sigma Aldrich) at a maximum load. Smoc-proline is activated by 3 equivalents 1-ethyl-3-(3-dimethylaminopropyl)carbodiimide (EDC) and 2 equivalents N-hydroxysuccinimide (NHS) in mixture of water and tetrahydrofuran (THF) 3:1 ratio (volume).

Thereafter, the ion exchanger loaded with the activated Smoc-proline is washed twice with water. After the washing step, 1.5 equivalents L-tyrosine methyl ester solved in water are added to the activated Smoc-proline and reacted at 24° C. for 12 minutes at pH 8 under agitation. Excess of L-tyrosine methyl ester and released NHS are removed by washing with water.

The yield in Example 7 is lower than the yield in Example 6.

The formed Pro-Tyr-OMe is released by deprotection using 0.5 mM NaOH (pH 10, 15 minutes) or $Na_2CO_3$ (pH 10, 20 minutes).

Example 8: Synthesis of Pro-Tyr-OMe

Smoc-proline is added to an ion exchange resin (Amberlite IRA-96; Sigma Aldrich) at a maximum load. Smoc-proline is activated by 3 equivalents 1-ethyl-3-(3-dimethylaminopropyl)carbodiimide (EDC) and 2 equivalents N-hydroxysuccinimide (NHS) in mixture of water and tetrahydrofuran (THF) 4:1 ratio (volume).

Thereafter, the ion exchanger loaded with the activated Smoc-proline is washed thrice with water. After the washing steps, 2 equivalents L-tyrosine methyl ester solved in water are added to the activated Smoc-proline and reacted at 15°

C. for 25 minutes at pH 8.2 under agitation. Excess of L-tyrosine methyl ester and released NHS are removed by washing with water.

The yield in Example 8 is similar to the yield in Example 7.

The formed Pro-Tyr-OMe is released by deprotection using 0.25M CaOH$_2$ (pH 10, 15 minutes) or CaCO$_3$ (pH 10, 30 minutes).

Example 9: Synthesis of Pro-Tyr-OMe

Smoc-proline is added to an ion exchange resin (Amberlite IRA-410; Sigma Aldrich) at a maximum load. Smoc-proline is activated by 3 equivalents 1-ethyl-3-(3-dimethylaminopropyl)carbodiimide (EDC) and 2 equivalents N-hydroxysuccinimide (NHS) in mixture of water and tetrahydrofuran (THF) 4:1 ratio (volume).

Thereafter, the ion exchanger loaded with the activated Smoc-proline is washed thrice with water. After the washing steps, 2 equivalents L-tyrosine methyl ester solved in water are added to the activated Smoc-proline and reacted at 15° C. for 25 minutes at pH 8.2 under agitation. Excess of L-tyrosine methyl ester and released NHS are removed by washing with water.

The yield in Example 9 is lower than the yield in Example 6.

The formed Pro-Tyr-OMe is released by deprotection using 1M NaOH (pH 10, 10 minutes) or Na$_2$CO$_3$ (pH 10, 20 minutes).

Example 10: Synthesis of Pro-Tyr-OMe

Smoc-Proline is added to an ion exchange resin (Amberlite IRA-958; Sigma Aldrich) at a maximum load. Smoc-Proline is activated by 3 equivalents 1-ethyl-3-(3-dimethylaminopropyl)carbodiimide (EDC) and 2 equivalents N-Hydroxysuccinimide (NHS) in mixture of water and tetrahydrofuran (THF) 4:1 ratio (volume).

Thereafter, the ion exchanger loaded with the activated Smoc-proline is washed thrice with water. After the washing steps, 2 equivalents L-tyrosine methyl ester solved in water are added to the activated Smoc-proline and reacted at 15° C. for 25 minutes at pH 8.2 under agitation. Excess of L-tyrosine methyl ester and released NHS are removed by washing with water.

The yield in Example 10 is higher than the yield in Example 10.

The formed Pro-Tyr-OMe is released by deprotection using 25% NH$_3$(aq) (pH 10, 20 minutes) or (NH$_4$)$_2$CO$_3$ (pH 10, 20 minutes).

Example 11: Synthesis of L-carnosine

Smoc-ß-alanine is added to an ion exchange resin (DEAE Sephadex A-25; GE Healthcare) at a maximum load. Smoc-ß-alanine is activated by 2-Ethoxy-1-ethoxycarbonyl-1,2-dihydroquinoline (EEDQ) in mixture of water and isopropyl alcohol 3:1 ratio (volume).

Thereafter, the ion exchanger loaded with the activated Smoc-ß-alanine is washed one time with water. After the washing step, 1.5 equivalent L-histidine solved in water are added to the activated Smoc-ß-alanine and reacted at 24° C. for 15 minutes at pH 7.8 under agitation. Excess of L-histidine and released NHS are removed by washing with water.

The yield in Example 11 is similar to the yield in Example 4.

The formed L-carnosine is released by deprotection using 0.5 M KOH (pH 9.8, 12 minutes) or K$_2$CO$_3$ (pH 10, 20 minutes).

Example 12: Synthesis of Smoc-Gly-His-OH

Smoc-glycine is added to an ion exchange resin (DEAE Sephadex A-25; GE Healthcare) at a maximum load. Smoc-glycine is obtained in a similar manner as disclosed above with regard to Smoc-ß-alanine (see Example 3). Smoc-glycine is activated by 3 equivalents 1-ethyl-3-(3-dimethylaminopropyl)carbodiimid (EDC) and 2 equivalents N-hydroxysuccinimide (NHS) in mixture of water and tetrahydrofuran (THF) 3:1 ratio (volume).

Thereafter, the ion exchanger loaded with the activated Smoc-glycine is washed thrice with water. After the washing steps, 1.5 equivalents L-histidine solved in water are added to the activated Smoc-glycine and reacted at 18° C. for 20 minutes at pH 8.5 under agitation. Excess of L-histidine and released NHS are removed by washing with water.

The formed Smoc-Gly-His-OH is released by eluting with 1M NaCl solution.

Example 13: Synthesis of Asn-Asn-OH

Smoc-Asn is added to an ion exchange resin (DEAE Sephadex A-25; GE Healthcare) at a maximum load. Smoc-Asn is obtained in a similar manner as disclosed above with regard to Smoc-ß-alanine (see Example 3). Smoc-Asn is activated by 3 equivalents 1-ethyl-3-(3-dimethylaminopropyl)carbodiimid (EDC) and 2 equivalents N-hydroxysuccinimide (NHS) in mixture of water and isopropyl alcohol 4:1 ratio (volume).

Thereafter, the ion exchanger loaded with the activated Smoc-Asn is washed three times with water. After the washing step, 1.5 equivalent L-Asn solved in water are added to the activated Smoc-Asn and reacted at 8° C. for 25 minutes at pH 8.7 under agitation. Excess of L-Asn and released NHS are removed by washing with water.

The formed Asn-Asn-OH is released by deprotection using 0.5M NaOH (pH 9.5, 12 minutes) or K$_2$CO$_3$ (pH 10, 25 minutes).

Example 14: Synthesis of Asn-Gln-OH

Smoc-Asn is added to an ion exchange resin (DEAE Sephadex A-25; GE Healthcare) at a maximum load. Smoc-Asn is activated by 3 equivalents 1-ethyl-3-(3-dimethylaminopropyl)carbodiimide (EDC) and 2 equivalent N-hydroxysuccinimide (NHS) in mixture of water and isopropyl alcohol 4:1 ratio (volume).

Thereafter the ion exchanger loaded with the activated Smoc-Asn is washed twice with water. After the washing steps, 1.5 equivalents L-Gln solved in water are added to the activated Smoc-Asn and reacted at 24° C. for 20 minutes at pH 9 under agitation. Excess of L-Gln and released NHS are removed by washing with water.

The formed Asn-Gln-OH is released by deprotection using 1M NaOH (pH 9.5, 12 minutes) or K$_2$CO$_3$ (pH 10, 25 minutes).

Example 15: Synthesis of Asp(OtBu)-Glu-OH

Smoc-Asp(OtBu)-OH is added to an ion exchange resin (DEAE Sephadex A-25; GE Healthcare) at a maximum load.

Smoc-Asp(OtBu)-OH is obtained in a similar manner as disclosed above with regard to Smoc-ß-alanine (see Example 3). Smoc-Asp(OtBu)-OH is activated by 3 equivalents 1-ethyl-3-(3-dimethylaminopropyl)carbodiimide (EDC) and 2 equivalents N-hydroxysuccinimide (NHS) in mixture of water and 2-methyltetrahydrofuran 4:1 ratio (volume).

Thereafter, the ion exchanger loaded with the activated Smoc-Asp(OtBu) is washed twice with water. After the washing steps, 1.5 equivalents L-Glu solved in water are added to the activated Smoc-Asp(OtBu) and reacted at 24° C. for 20 minutes at pH 9 under agitation. Excess of L-Glu and released NHS are removed by washing with water.

The formed Asp(OtBu)-Glu-OH is released by deprotection using 1M NaOH (pH 9.5, 12 minutes) or $K_2CO_3$ (pH 10, 25 minutes).

Example 16: Synthesis of Ile-D-Val-OH

Smoc-Ile-OH is added to an ion exchange resin (DEAE Sephadex A-25; GE Healthcare) at a maximum load. Smoc-Ile-OH is obtained in a similar manner as disclosed above with regard to Smoc-ß-alanine (see Example 3). Smoc-Ile-OH is activated by 4 equivalents 1-ethyl-3-(3-dimethylaminopropyl)carbodiimid (EDC) and 3 equivalents N-hydroxysuccinimide (NHS) in mixture of water and dimethyl sulfoxide (DMSO) 3:1 ratio (volume).

Thereafter, the ion exchanger loaded with the activated Smoc-Ile is washed twice with water. After the washing steps, 1.5 equivalents D-Val solved in water are added to the activated Smoc-Ile and reacted at 25° C. for 17 minutes at pH 8.5 under agitation. Excess of D-Val and released NHS are removed by washing with water.

The formed Ile-D-Val-OH is released by deprotection using 1M NaOH (pH 9.5, 12 minutes) or $Na_2CO_3$ (pH 10, 25 minutes).

Example 17: Synthesis of Sulfmoc-Gly-Val-OH 9-(2-Sulfo)fluorenylmethyloxycarbonylglycine (Sulfmoc-Gly-OH) is obtained in a similar manner as disclosed above with regard to Smoc-ß-alanine (see Example 3). 9-(2-Sulfo)fluorenylmethyloxycarbonylglycine (Sulfmoc-Gly-OH) is activated by 3 equivalents 1-ethyl-3-(3-dimethylaminopropyl)carbodiimid (EDC) and 2 equivalents N-hydroxysuccinimide (NHS) in water. Afterwards, the preactivated Sulfmoc-Gly is loaded to an ion exchange resin (DEAE Sephadex A-25; GE Healthcare).

Thereafter, the ion exchanger loaded with the activated Sulfmoc-Gly is washed twice with water. After the washing steps, 1.5 equivalents L-Val solved in water are added to the activated Sulfmoc-Gly and reacted at 25° C. for 30 minutes at pH 9 under agitation. Excess of L-Val and released NHS are removed by washing with water.

The formed Sulfmoc-Gly-Val-OH is released by eluting with 1M NaCl solution.

Example 18: Synthesis of Ile-Pro-Phe-OH

Smoc-Ile-OH is added to an ion exchange resin (DEAE Sephadex A-25; GE Healthcare) at a maximum load. Smoc-Ile-OH is activated by 3 equivalents 1-ethyl-3-(3-dimethylaminopropyl)carbodiimide (EDC) and 2 equivalents N-hydroxysuccinimide (NHS) in mixture of water and acetonitrile (MeCN) 3:1 ratio (volume).

Thereafter, the ion exchanger loaded with the activated Smoc-Ile is washed twice with water. After the washing steps, 1.5 equivalents L-Pro solved in water are added to the activated Smoc-Ile and reacted at 25° C. for 12 minutes at pH 8.5 under agitation. Excess of L-Pro and released NHS are removed by washing with water. Smoc-Ile-Pro-OH is activated by 2.5 equivalents 1-ethyl-3-(3-dimethylaminopropyl)carbodiimide (EDC) and 1.2 equivalents N-hydroxysuccinimide (NHS) in mixture of water and acetonitrile (MeCN) 3:1 ratio (volume). Thereafter, the ion exchanger loaded with the activated Smoc-Ile-Pro is washed twice with water. After the washing steps, 1.5 equivalents L-Phe solved in water are added to the activated Smoc-Ile-Pro and reacted at 25° C. for 12 minutes at pH 8.6 under agitation. Excess of L-Phe and released NHS are removed by washing with water. The formed Ile-Pro-Phe-OH is released by deprotection using 1M NaOH (pH 9.5, 12 minutes) or $Na_2CO_3$ (pH 10, 25 minutes).

Example 19: Synthesis of Ile-Val-Phe-OH

Smoc-Ile-OH is added to an ion exchange resin (DEAE Sephadex A-25; GE Healthcare) at a maximum load. Smoc-Ile-OH is activated by 3 equivalents 1-ethyl-3-(3-dimethylaminopropyl)carbodiimide (EDC) and 2 equivalents N-hydroxysuccinimide (NHS) in mixture of water and acetonitrile (MeCN) 3:1 ratio (volume).

Thereafter, the ion exchanger loaded with the activated Smoc-Ile is washed twice with water. After the washing steps, 1.5 equivalents L-Val solved in water are added to the activated Smoc-Ile and reacted at 25° C. for 12 minutes at pH 8.5 under agitation. Excess of L-Val and released NHS are removed by washing with water. Smoc-Ile-Val-OH is activated by 2.5 equivalents 1-ethyl-3-(3-dimethylaminopropyl)carbodiimide (EDC) and 1.2 equivalents N-hydroxysuccinimide (NHS) in mixture of water and acetonitrile (MeCN) 3:1 ratio (volume). Thereafter, the ion exchanger loaded with the activated Smoc-Ile-Val is washed twice with water. After the washing steps, 1.5 equivalents L-Phe solved in water are added to the activated Smoc-Ile-Val and reacted at 25° C. for 12 minutes at pH 8.6 under agitation. Excess of L-Phe and released NHS are removed by washing with water. The formed Ile-Val-Phe-OH is released by deprotection using 1M NaOH (pH 9.5, 12 minutes) or $Na_2CO_3$ (pH 10, 25 minutes).

Example 20: Synthesis of Ile-His-Ile-OH

Smoc-Ile-OH is added to an ion exchange resin (DEAE Sephadex A-25; GE Healthcare) at a maximum load. Smoc-Ile-OH is activated by 3 equivalents 1-ethyl-3-(3-dimethylaminopropyl)carbodiimide (EDC) and 2 equivalents N-hydroxysuccinimide (NHS) in mixture of water and acetonitrile (MeCN) 3:1 ratio (volume).

Thereafter, the ion exchanger loaded with the activated Smoc-Ile is washed twice with water. After the washing steps, 1.5 equivalents L-His solved in water are added to the activated Smoc-Ile and reacted at 25° C. for 10 minutes at pH 8.2 under agitation. Excess of L-His and released NHS are removed by washing with water. Smoc-Ile-His-OH is activated by 2.5 equivalents 2-Ethoxy-1-ethoxycarbonyl-1, 2-dihydroquinoline in mixture of water and acetonitrile (MeCN) 3:1 ratio (volume). Thereafter, the ion exchanger loaded with the activated Smoc-Ile-His is washed twice with water. After the washing steps, 1.5 equivalents L-Ile solved in water are added to the activated Smoc-Ile-His and reacted at 25° C. for 10 minutes at pH 8.5 under agitation. Excess of L-Ile and released 1,2-dihydroquinoline and ethanol are removed by washing with water. The formed Ile-His-Ile-OH is released by deprotection using 1M NaOH (pH 9.5, 12 minutes) or Na$_2$CO$_3$ (pH 10, 25 minutes).

Example 21: Synthesis of Leu-Ile-His-OH

Smoc-Ile-OH is added to an ion exchange resin (DEAE Sephadex A-25; GE Healthcare) at a maximum load. Smoc-Ile-OH is activated by 3 equivalents 1-ethyl-3-(3-dimethylaminopropyl)carbodiimide (EDC) and 2 equivalents N-hydroxysuccinimide (NHS) in mixture of water and acetonitrile (MeCN) 3:1 ratio (volume).

The formed Ile-His-OH is released by deprotection using organic base like ethanolamine, N,N-diisopropylethylamine, triethylamine or 5% N-methyl-morpholinew Ile-His is precipitated by adding aprotic solvents and washed till base residues are removed.

Thereafter, the ion exchanger is regenerated with 1M NaCl solution and washed twice with water. Smoc-Ile-OH is added to the ion exchange resin at a maximum load and is activated by 3 equivalents 1-ethyl-3-(3-dimethylaminopropyl)carbodiimide (EDC) and 2 equivalents N-hydroxysuccinimide (NHS) in mixture of water and acetonitrile (MeCN) 3:1 ratio (volume). Thereafter, the ion exchanger loaded with the activated Smoc-Leu is washed twice with water. After the washing steps, 1 equivalents L-Ile-His solved in water are added to the activated Smoc-Leu and reacted at 25° C. for 10 minutes at pH 8.5 under agitation. Released NHS is removed by washing with water. The formed Leu-Ile-His-OH is released by deprotection using 1M NaOH (pH 9.5, 12 minutes) or Na$_2$CO$_3$ (pH 10, 25 minutes).

Example 22: Synthesis of LAGV-OH (SEQ ID NO: 1)

Smoc-Ile-OH is added to an ion exchange resin (DEAE Sephadex A-25; GE Healthcare) at a maximum load. Smoc-Leu-OH is activated by 3 equivalents 1-ethyl-3-(3-dimethylaminopropyl)carbodiimide and 2 equivalents N-hydroxysuccinimide (NHS) in mixture of water and isopropanole 2:1 ratio (volume).

Thereafter, the ion exchanger loaded with the activated Smoc-Ile is washed with water. After the washing step, 1.5 equivalents L-Ala solved in water are added to the activated Smoc-Leu and reacted at 25° C. for 10 minutes at pH 7 under agitation. Excess of L-Ala and released NHS are removed by washing with water. Smoc-Leu-Ala-OH is activated by 2.5 equivalents 1-ethyl-3-(3-dimethylaminopropyl)carbodiimide and 2 equivalents N-hydroxysuccinimide in mixture of water and isopropanole 2:1 ratio (volume). Thereafter, the ion exchanger loaded with the activated Smoc-Leu-Ala is washed twice with water. After the washing steps, 1.5 equivalents Gly solved in water are added to the activated Smoc-Leu-Ala and reacted at 25° C. for 10 minutes at pH 7 under agitation. Excess of Gly and released NHS are removed by washing with water. Smoc-LAG-OH is activated by 2.5 equivalents 1-ethyl-3-(3-dimethylaminopropyl)carbodiimid and 2 equivalents N-hydroxysuccinimide in mixture of water and isopropanole 2:1 ratio (volume). Thereafter, the ion exchanger loaded with the activated Smoc-LAG is washed twice with water. After the washing steps, 1.5 equivalents Val solved in water are added to the activated Smoc-LAG and reacted at 25° C. for 15 minutes at pH 7 under agitation. Excess of Val and released NHS are removed by washing with water.

The formed LAGV-OH (SEQ ID NO: 1) is released by deprotection using NaOH (pH 10, 20 minutes) or Na$_2$CO$_3$ (pH 10, 25 minutes). Yield: 20%.

Example 23: Synthesis of Leu-Enkephalin (YGGFL (SEQ ID NO: 2))

Smoc-Tyr-OH is obtained in a similar manner as disclosed above with regard to Smoc-ß-alanine (see Example 3). Smoc-Tyr-OH is added to an ion exchange resin (DEAE Sephadex A-25; GE Healthcare) at a maximum load. Smoc-Tyr-OH is activated by 3 equivalents 1-ethyl-3-(3-dimethylaminopropyl)carbodiimide and 2 equivalents N-hydroxysuccinimide (NHS) in mixture of water and MeCN 2:1 ratio (volume).

Thereafter, the ion exchanger loaded with the activated Smoc-Tyr is washed with water. After the washing step, 1.5 equivalents Gly solved in water are added to the activated Smoc-Tyr and reacted at 25° C. for 10 minutes at pH 7 under agitation. Excess of Gly and released NHS are removed by washing with water. Smoc-YG-OH is activated by 2.5 equivalents 1-ethyl-3-(3-dimethylaminopropyl)carbodiimide and 2 equivalents N-hydroxysuccinimide in mixture of water and MeCN 2:1 ratio (volume). Thereafter, the ion exchanger loaded with the activated Smoc-YG is washed with water. After the washing steps, 1.5 equivalents Gly solved in water are added to the activated Smoc-YG and reacted at 25° C. for 10 minutes at pH 7 under agitation. Excess of Gly and released NHS are removed by washing with water. This Procedure is repeated for each step until the complete sequence of Smoc-YGGFL-OH (SEQ ID NO: 2) is synthesized.

The formed YGGFL-OH (SEQ ID NO: 2) is released by deprotection using NaOH (pH 10, 20 minutes) or Na$_2$CO$_3$ (pH 10, 25 minutes). Yield: 19%.

Example 24: Synthesis of Leu-Enkephalin (YGGFL (SEQ ID NO: 2)) on SPPS

Tyr(tBu)-OH is added to an solid phase peptide resin (TentaGel® S TRT Cl Resin; 0.2-0.3 mmol/g) at a maximum load via the amine function. SolidS-Tyr(tBu)-OH is activated by 4 equivalents 1-ethyl-3-(3-dimethylaminopropyl) carbodiimide hydrochloride and 3 equivalents Ethyl cyano (hydroxyimino)acetat (Oxyma) in mixture of water and MeCN 2:1 ratio (volume).

Thereafter, the solid support loaded with the activated Tyr(tBu) is washed with water. After the washing step, 3 equivalents Gly solved in water are added to the activated SolidS-Tyr(tBu) and reacted at 25° C. for 30 minutes at pH 8 under agitation. Excess of Gly and released Oxyma are removed by washing with water. SolidS-YG-OH is activated by 4 equivalents 1-ethyl-3-(3-dimethylaminopropyl)carbodiimide hydrochloride and 3 equivalents Ethyl cyano(hydroxyimino)acetat (Oxyma) in mixture of water and MeCN 2:1 ratio (volume). Thereafter, solid support loaded with the activated Smoc-YG is washed with water. After the washing steps, 3 equivalents Gly solved in water are added to the activated SolidS-YG and reacted at 25° C. for 30 minutes at pH 8 under agitation. Excess of Gly and released Oxyma are removed by washing with water. This procedure is repeated for each step until the complete sequence of SolidS-YGGFL-OH (SEQ ID NO: 2) is synthesized.

The formed YGGFL-OH (SEQ ID NO: 2) is cleaved from solid support by using 95% trifluoroacetic acid (TFA) for 1.5 h. Yield: 30.5%.

Example 25: Synthesis of Acetyl Hexapeptide-3 (EEMQRR-OH (SEQ ID NO:3)) on SPPS Glu(OtBu)-OH is added to an solid phase peptide resin (TentaGel® S TRT Cl Resin; 0.2-0.3 mmol/g) at a maximum load via the amine function. SolidS-Glu(OtBu)-OH is activated by 4 equivalents 1-ethyl-3-(3-dimethylaminopropyl) carbodiimide hydrochloride and 3 equivalents Ethyl cyano (hydroxyimino)acetate (Oxyma) in mixture of water and MeCN 2:1 ratio (volume).

Thereafter, the solid support loaded with the activated Glu(OtBu) is washed with water. After the washing step, 3 equivalents Glu(OtBu) solved in water are added to the activated SolidS-Glu(OtBu) and reacted at 25° C. for 30 minutes at pH 8 under agitation. Excess of Glu(OtBu) and released Oxyma are removed by washing with water. SolidS-EE-OH is activated by 4 equivalents 1-ethyl-3-(3-dimethylaminopropyl)-carbodiimide hydrochloride and 3 equivalents Ethyl cyano(hydroxyimino)acetate (Oxyma) in mixture of water and MeCN 2:1 ratio (volume). Thereafter, solid support loaded with the activated SolidS-EE is washed with water. After the washing steps, 3 equivalents Met solved in water are added to the activated SolidS-EE and reacted at 25° C. for 30 minutes at pH 8 under agitation. Excess of Met and released Oxyma are removed by washing with water. This procedure is repeated for each step until the complete sequence of SolidS-EEMQRR-OH (SEQ ID NO: 3) is synthesized. Arginine was used without side chain protecting groups.

The formed EEMQRR-OH (SEQ ID NO: 3) is cleaved from solid support and side chain deprotected by using 95% Trifluoroacetic acid (TFA) for 1.5 h. Yield: 32%.

Example 26: Synthesis of Deca-Ala (SEQ ID NO: 4) on SPPS

Ala-OH is added to an solid phase peptide resin (TentaGel® S TRT Cl Resin; 0.2-0.3 mmol/g) at a maximum load via the amine function. SolidS-Ala-OH is activated by 4 equivalents 1-ethyl-3-(3-dimethylaminopropyl)carbodiimide hydrochloride and 3 equivalents Ethyl cyano(hydroxyimino)acetat (Oxyma) in mixture of water and MeCN 2:1 ratio (volume).

Thereafter, the solid support loaded with the activated SolidS-Al is washed with water two times. After the washing steps, 3 equivalents Ala solved in water are added to the activated SolidS-Ala-OH and reacted at 25° C. for 30 minutes at pH 8 under agitation. Excess of Ala and released Oxyma are removed by washing with water. SolidS-AA-OH is activated by 4 equivalents 1-ethyl-3-(3-dimethylaminopropyl)-carbodiimide hydrochloride and 3 equivalents Ethyl cyano(hydroxyimino)acetat (Oxyma) in mixture of water and MeCN 2:1 ratio (volume). Thereafter, solid support loaded with the activated SolidS-AA is washed with water. After the washing steps, 3 equivalents Ala solved in water are added to the activated SolidS-AA and reacted at 25° C. for 30 minutes at pH 8 under agitation. Excess of Ala and released Oxyma are removed by washing with water. This procedure is repeated for each step until the complete sequence of SolidS-decaAla-OH is synthesized.

The formed Deca-Ala-OH (SEQ ID NO: 4) is cleaved from solid support by using 95% Trifluoroacetic acid (TFA) for 1.5 h. Yield: 17%.

Example 27: Synthesis of L-carnosine 4-(((L-histidyl)oxy)methyl)-N,N,N-trimethylbenzenaminium is added to an ion exchange resin (SP Sephadex C-25; GE Healthcare) at a maximum load. Smoc-ß-alanine is activated by 3 equivalent 1-ethyl-3-(3-dimethylaminopropyl)carbodiimide (EDC) and 2 equivalents N hydroxysuccinimide (NHS) in mixture of water and isopropanol 4:1 ratio (volume). Thereafter the activated Smoc-ß-alanine-NHS ester is added to Histidine on the ion exchange column. The mixture is allowed to react for 15 min at pH 7.5 under agitation. Thereafter, the ion exchanger loaded with the Smoc-ß-Ala-His is washed two times with water to remove the excess of Smoc-ß-alanine and released NHS. Afterwards, the Smoc-protecting group is removed by 5% piperazine in water and washed two times with water. The formed L-carnosine is released by deprotection using 98% TFA.

The invention claimed is:

1. A method for preparing peptides, the method comprising a step of forming a peptide bond, wherein a carboxyl group of a first amino acid or a first peptide is activated and an amino group of said first amino acid or said first peptide is protected, and said activated carboxyl group of said first amino acid or said first peptide is reacted with an amino group of a second amino acid or a second peptide wherein said carboxyl group of said first amino acid or said first peptide is activated in the absence of said second amino acid or said second peptide, wherein said forming of a peptide bond is achieved while said first amino acid or said first peptide is ionically bound to an ion exchanger or covalently bound to a solid phase, wherein any reactive side chain functional group of said first amino acid or said first peptide and/or said second amino acid or said second peptide is protected with a side chain protecting group, and wherein a carboxyl group of said second amino acid or said second peptide being reacted with said first activated amino acid or said activated first peptide is not protected.

2. The method according to claim 1, wherein said amino group of said first amino acid or said first peptide is protected by a protecting group having a water-solubility enhancing group.

3. The method according to claim 2, wherein said protecting group having a water-solubility enhancing group comprises at least two water-solubility enhancing groups.

4. The method according to claim 3, wherein said protecting group having a water-solubility enhancing group comprises at least two ionic groups.

5. The method according to claim 2, wherein said protecting group having a water-solubility enhancing group comprises exactly one water-solubility enhancing group.

6. The method according to claim 1, wherein said amino group of said first amino acid or said first peptide is protected by a solid phase.

7. The method according to claim 1, wherein said side chain functional group being protected is selected from α-amino, side chain amino, thiol, carboxyl, hydroxyl, phosphono, and seleno.

8. The method according to claim 1, wherein said activation of said carboxyl group of said first amino acid or said first peptide and/or said reaction of said activated carboxyl group of said first amino acid or said first peptide with said amino group of said second amino acid or said second peptide is achieved using an environmentally friendly solvent.

9. The method according to claim 8, wherein said environmentally friendly solvent comprises a non-protic organic solvent and/or a secondary alcohol and/or a tertiary alcohol.

10. The method according to claim 9, wherein said environmentally friendly solvent comprises a non-protic organic solvent.

11. The method according to claim 1, wherein said forming of the peptide bond is achieved in solution having no strong basic condition.

12. The method according to claim 11, wherein said forming of the peptide bond is achieved in solution at a pH below 12, or below 10.

13. The method according to claim 11, wherein said forming of the peptide bond is achieved in solution at a pH value in a range of 4 to 12, or in a pH range of 6 to 10, or in a pH range of 7 to 9.5, or in a pH range of 7 to 9.0, or in a pH range of 7 to 8.5.

14. The method according to claim 1, wherein said carboxyl group of said first amino acid or said first peptide is activated by a coupling agent.

15. The method according to claim 1, wherein said first amino acid or said first peptide is ionically contacted with an ion exchanger.

16. The method according to claim 1, wherein said side chain protecting group protects a side chain group of an amino acid selected from the group consisting of Glutamic acid (Glu), Aspartic acid (Asp), Cysteine (Cys), Lysine (Lys), Serine (Ser), and Threonine (Thr).

17. The method according to claim 1, wherein said carboxyl group of said first amino acid or said first peptide is activated by a coupling agent while said first amino acid or said first peptide is ionically bound to an ion exchanger or covalently bound to a solid phase.

18. The method according to claim 1, wherein said protection of said first amino acid, of said first peptide, of said second amino acid, and/or of said second peptide is achieved by reacting said first amino acid, said first peptide, said second amino acid, and/or said second peptide with a protective agent comprising I. a backbone structure, II. at least one water-solubility enhancing group, and III. at least one reactive group, wherein the backbone structure comprises at least one moiety selected from the group consisting of 9-methylfluorene, t-butane, and mono-, and di- or triphenylmethane, wherein the water-solubility enhancing group is selected from the group consisting of $SO_3^-$, $PO_3^{2-}$, $N(CH_3)_2$, $N(CH_3)_3^+$, CN, $OSO_3^-$ ester, $OPO_3^{2-}$ ester, and combinations thereof, and wherein the water-solubility enhancing group and the reactive group are attached to the backbone structure via at least one covalent bond.

19. The method according claim 1, wherein said side chain protecting group comprises at least one water solubility enhancing functional group.

20. The method according claim 19, wherein said water solubility enhancing functional group is an ionic group.

21. The method according to claim 1, wherein said forming of a peptide bond is achieved while said first amino acid or said first peptide is ionically bound to an ion exchanger and after forming said peptide bond the obtained peptide is removed from the ion exchanger by deprotecting said obtained peptide.

22. The method according to claim 21, comprising removing at least 50% of side chain protecting groups that are attached to amino acids in a target said obtained peptide by a cleaving composition.

* * * * *

UNITED STATES PATENT AND TRADEMARK OFFICE
CERTIFICATE OF CORRECTION

PATENT NO. : 11,976,094 B2
APPLICATION NO. : 17/705607
DATED : May 7, 2024
INVENTOR(S) : Sascha Knauer Page 1 of 1

It is certified that error appears in the above-identified patent and that said Letters Patent is hereby corrected as shown below:

In the Claims

At Column 58, Line 4, Claim 19 "according claim" should be -- according to claim --.

At Column 58, Line 7, Claim 20 "according claim" should be -- according to claim --.

At Column 58, Line 16, Claim 22 "acids in a target" should be -- acids in --.

Signed and Sealed this
Fourth Day of February, 2025

Coke Morgan Stewart
*Acting Director of the United States Patent and Trademark Office*

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Leu Ala Gly Val
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Tyr Gly Gly Phe Leu
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Glu Glu Met Gln Arg Arg
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Ala Ala Ala Ala Ala Ala Ala Ala Ala Ala
1               5                   10
```